United States Patent [19]

Tsang et al.

[11] Patent Number: 4,983,589
[45] Date of Patent: Jan. 8, 1991

[54] FUNGICIDAL IMIDAZOLE DIPHENYLALIPHATICBORANES AND DERIVATIVES THEREOF

[75] Inventors: Tsze H. Tsang, El Cerrito; Vincent J. Spadafora, Benicia; Patricia Pomidor, Orinda, all of Calif.

[73] Assignee: Chevron Research and Technology Company, San Francisco, Calif.

[21] Appl. No.: 450,872

[22] Filed: Dec. 14, 1989

[51] Int. Cl.$^5$ .................... A01N 55/08; C07F 5/02
[52] U.S. Cl. ............................. 514/64; 548/110
[58] Field of Search ..................... 548/110; 514/64

[56] References Cited

U.S. PATENT DOCUMENTS

| | | | |
|---|---|---|---|
| 3,062,708 | 11/1962 | Updegraff | 167/30 |
| 3,211,679 | 10/1965 | Updegraff | 260/19 |
| 3,268,401 | 8/1966 | Birmbaum et al. | 167/38 |
| 3,686,398 | 8/1972 | Kohn et al. | 424/185 |
| 3,696,103 | 10/1972 | Cometti | 260/268 |
| 4,613,373 | 9/1986 | Umeno | 106/183 |

FOREIGN PATENT DOCUMENTS 62-277307  5/1986  Japan .

OTHER PUBLICATIONS

Derwent Abstract 5188957 WPI Acc No: 89-110641/15 (6-1989).
Compte Rendus Hebdomadaires des Seances de l'Academie des Sciences, p. 319, vol. 254, (1962).

*Primary Examiner*—Richard L. Raymond
*Attorney, Agent, or Firm*—R. C. Gaffney; L. S. Squires

[57] ABSTRACT

Organoborane Imidazole compounds having the formula:

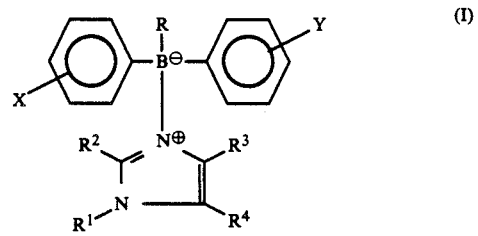

wherein R, $R^1$, $R^2$, $R^3$, $R^4$, and X are defined in the description, and intermediates therefor are disclosed.

The compounds of formula I are especially useful as agricultural fungicides.

65 Claims, No Drawings

FUNGICIDAL IMIDAZOLE DIPHENYLALIPHATICBORANES AND DERIVATIVES THEREOF

BACKGROUND OF THE INVENTION

This invention relates to certain diphenylaliphatic borane imidazole complexes and derivatives thereof. In a further aspect, the invention relates to the use of such complexes as agricultural fungicides.

A large amount of crop loss and plant damage is incurred each year due to plant diseases caused by four classes of fungi: Ascomycetes, causing a large number of leaf spots, blights, soil-bourn and post-harvest diseases; Deuteromycetes, also causing a large number of leaf spots, blights, soil-bourn and post-harvest diseases; Basidiomycetes, causing rust, smuts, bunts and soil borne-diseases; and Phycomycetes, causing downy mildews, leaf blights and soil-bourn diseases.

Leaf spot and blight diseases, such as those induced by species of Leptosphaeria, Mycosphaerella, Alternaria, and Helminthosporium cause damage to many crops such as maize, wheat, banana, and solanaceous crops and are difficult to control.

Various species of the genus Botrytis are responsible for diseases causing large losses in numerous vegetable, ornamental and vine crops. Present fungicides such as benzimidazoles and dicarboximides cannot adequately control these diseases due to the development of resistance by the pathogen.

The late blights and downy mildew plant diseases produced, for example, by Phytophthora and Plasmopara are very destructive to grape and solanaceous crops, e.g., potato, tomato. These diseases are also difficult to control due to the development of resistance to the leading systemic fungicides used to control these diseases.

Thus, it would be desirable to develop new fungicides which are effective to control plant diseases and especially in the case of late blights, mildew and Botrytis-produced diseases which are not subject to cross-resistance of the pathogen and which do not cause significant injury to the plants (i.e., are relatively non-phytotoxic).

U.S. Pat. No. 3,062,708 generally teaches that amine complexes of triphenylborane with certain Lewis bases have antifungal activity. The patent shows in vitro activity with respect to triphenylborane-imidazole and illustrates in vivo activity against tomato early blight, bean rust, late blight and seed rot (*Pythium ultimum*) with respect to certain triphenylborane amines including complexes with piperidine, pyridine and 4-ethylpyridine.

U.S. Pat. No. 3,211,679 teaches that triarylborane amine complexes with pyridine or a variety of substituted pyridines are useful as toxicants for antifouling paint and that such paints import residual toxicity to marine borers to wood structures.

U.S. Pat. No. 3,686,398 teaches that certain 10,9-boroxarophenanthrenes are useful to control fungi and exhibited preventative control of bean rust and celery late blight.

U.S. Pat. No. 3,696,103 teaches that certain di(substituted and unsubstituted phenyl)azaborolidines exhibit fungicidal, insecticidal, acaricidal and herbicidal activity. The fungicidal activity is described as polyvalent and is shown against bean anthracnose (*Collectrotrichum lindemythianum*), tomato mildew (late blight) (*Phytophthora infestans*), tobacco mildew (blue mold) (*Peronospora tabaci*), cucumber (powdery) mildew (*Erysiphe cichoracearum*) and wheat rust (*Puccinia glumarum*) at quantities of between 10 and 200 g of active substance per hectoliter of liquid diluent such as water.

U.S. Pat. No. 4,613,373 teaches that certain tetra(substituted and unsubstituted phenyl) boranes complexed with a heterocyclic amine are useful as antifouling, antiseptic, and antifungal agents in many industrial applications. In vitro inhibiting activity of certain of patentees compounds against certain fungi are shown in Table 4 of the patent.

Based on the Derwent Abstract, Japanese Patent Application Publication 62-277307 describes complexes of tri(substituted phenyl)borane with amines and nitrogen containing heterocycles as useful as insecticides, miticides and nematocides. Based on Derwent Abstract 5188957, Japanese Patent Application publication JP 1056684 published Mar. 3, 1989 discloses certain tetraphenylboron-onium complexes useful as agricultural and industrial fungicides.

SUMMARY OF THE INVENTION

The present invention provides compounds having fungicidal activity against certain plant diseases and which exhibit no crop phytotoxicity or low levels of phytotoxicity which are within acceptable limits. Certain of the compounds exhibit protective or preventative activity against a broad spectrum of Botrytis diseases, mildews and blights and leafspot and leaf blights induced by Septoria, and are not affected by cross-resistance of the pathogen to other fungicides. Certain of the compounds further exhibit eradicant activity with respect to certain fungal diseases, for example, celery late blight.

The present invention provides organoborane imidazole complexes having the following formula (I) and intermediates of formula II hereinbelow:

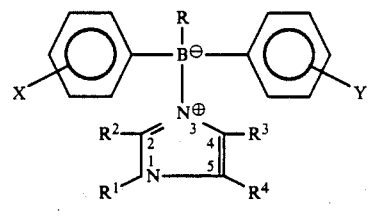

and

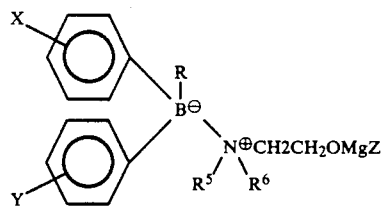

wherein:

R is alkyl having 1 through 4 carbon atoms; cycloalkyl having 3 through 6 carbon atoms; alkenyl having 2 through 6 carbon atoms; haloalkyl having 1 through 4 carbon atoms and 1 through 4 halo substituent independently selected from the group of fluoro, chloro, and bromo; or haloalkenyl having 3 through 6 carbon atoms and 1 through 4 halo atoms independently selected from the group of fluoro, chloro and bromo;

$R^1$ is hydrogen; alkyl having 1 through 12 carbon atoms; cycloalkyl having 3 through 6 carbon atoms; lower alkenyl having 2 through 6 carbon atoms; haloalkyl having 1 through 4 carbon atoms and 1 through 3 halo atoms independently selected from the group of fluoro, chloro, bromo and iodo; haloalkenyl having 2 through 6 carbon atoms and 1 through 3 halo atoms independently selected from the group of fluoro, chloro, bromo and iodo; cyanoalkyl wherein the alkyl moiety has 1 through 4 carbon atoms, hydroxyalkyl having 1 through 6 carbon atoms and 1 hydroxy group preferably located at the terminal carbon atom of the alkyl group, lower alkoxyalkyl having 1 through 3 carbon atoms in the alkoxy moiety and 1 through 3 carbon atoms in the alkyl moiety, lower alkoxycarbonylalkyl having 1 through 3 carbon atoms in the alkoxy moiety and 1 through 3 carbon atoms in the alkyl moiety; phenyl; substituted phenyl having 1 through 4 substituents independently selected from the group of fluoro, chloro, bromo, iodo, lower alkyl having 1 through 6 carbon atoms and nitro with the proviso that said substituted phenyl has no more than two nitro substituents; aralkyl having 1 through 4 carbon atoms in the alkyl moiety and wherein the aryl moiety is phenyl; substituted benzyl having 1 through 4 substituents on the phenyl moiety independently selected from the group of fluoro, chloro, bromo, iodo, lower alkyl having 1 through 6 carbon atoms and nitro with the proviso that said phenyl moiety has no more than two nitro substituents; and 1,3-dioxolan-2-yl-alkyl in which the alkyl moiety has 1 through 4 carbon atoms;

$R^2$ is hydrogen; lower alkyl having 1 through 6 carbon atoms; phenyl, benzyl; or substituted benzyl having 1 through 4 substituents on the phenyl ring independently selected from the group of fluoro, chloro, bromo, iodo and alkyl having 1 through 6 carbon atoms;

$R^3$ is hydrogen or alkyl having 1 through 6 carbon atoms with the proviso that when $R^4$ is other than alkyl, then $R^3$ is hydrogen;

$R^4$ is hydrogen, alkyl having 1 through 6 carbon atoms, phenyl, or phenalkyl in which the alkyl moiety has 1 through 4 carbon atoms with the proviso that at least two of $R^1$, $R^2$, $R^3$ and $R^4$ are hydrogen and the further proviso that when $R^3$ is alkyl, then $R^4$ is an alkyl group identical to the $R^3$ alkyl group;

$R^5$ and $R^6$ are independently hydrogen or lower alkyl having 1 through 6 carbon atoms; and X and Y are independently selected from the group of hydrogen, alkyl having 1 through 4 carbon atoms; fluoro; chloro; alkoxy having 1 through 4 carbon atoms; alkylthio having 1 through 4 carbon atoms; or haloalkyl having 1 through 4 carbon atoms and 1 through 3 halo substituents independently selected from the group of fluoro, chloro, and bromo and may be at any available position on the respective phenyl rings.

In those cases where the complex of Formula I or the intermediates of formula II have an asymmetric carbon atom, the compounds can exist as optical isomers. In some instances the compounds also exist as geometric isomers, for example, where R is an alkenyl group having a cis-trans double bond. In some cases (e.g., where $R^1 = H$ and $R^3 \neq R^4$), the compounds can exist as coordination isomers wherein boron is coordinated to either the N1 or N3 nitrogen.

The above formulas are intended to encompass the respective individual isomers as well as mixtures thereof and the respective isomers as well as mixtures thereof are encompassed within the invention.

In a further aspect, the invention provides a fungicidal composition comprising a compatible carrier and a fungicidally effective amount of the compound(s) of the invention or mixtures thereof.

The invention also provides a method for preventing or controlling fungi, which comprises applying an amount of a compound of Formula I or mixtures thereof to such fungi or its habitat which is effective to prevent or inhibit or arrest the growth of the fungi.

In another aspect the invention provides a method for preventing or controlling fungal plant diseases which comprises applying to the plant an amount of the compound(s) of Formula I or mixtures thereof which is effective to prevent or inhibit the growth of the fungal pathogen producing the disease.

The present invention also provides chemical intermediates, e.g., the compound of formula II, and processes for preparing the compounds of Formula I.

The invention will be further described hereinbelow.

FURTHER DESCRIPTION OF THE INVENTION AND THE PREFERRED EMBODIMENTS

Illustrations of typical compounds of Formula I can be had by reference to Examples 1–6 set forth hereinbelow on Pages 23–72.

In terms of fungicidal effectiveness and spectrum of activity, the preferred compounds are those wherein $R^1$ is hydrogen, alkyl having 1 through 6 carbon atoms, preferably 1 through 4 carbon atoms, alkenyl having 2 through 6 carbon atoms, haloalkenyl having 2 through 6 carbon atoms and 1 through 3 halo atoms independently selected from the group of fluoro, chloro, and bromo, lower hydroxyalkyl having 1 through 3 carbon atoms and 1 hydroxy group, phenyl or aralkyl having 1 through 4 carbon atoms in the alkyl moiety and the aryl moiety is phenyl; $R^2$, $R^3$ and $R^4$ are independently hydrogen or alkyl having 1 through 6, preferably 1 through 3, carbon atoms; and X is hydrogen, alkyl having 1 through 4 carbon atoms, with the proviso that at least two of $R^1$, $R^2$, $R^3$ or $R^4$ are hydrogen.

Especially preferred in terms of the magnitude of antifungal activity or spectrum of antifungal activity, and/or crop safety are those compounds wherein R is alkyl or alkenyl, especially methyl and vinyl; $R^1$ is hydrogen or is an alkyl, cycloalkyl, alkenyl group having four or less carbon atoms, 2-hydroxyethyl or 2,2,2-trifluoroethyl and especially isopropyl, sec-butyl, t-butyl, cyclopropyl vinyl 2-hydroxyethyl and 2,2,2-trifluoroethyl; $R^2$ is hydrogen. Also, in the case where $R^1$, $R^3$, $R^4$, X and Y are all hydrogen the compounds where $R^1$ is alkyl having 1 through 4 carbon atoms generally exhibit good fungicidal activity.

The following compounds exhibit exceptionally excellent activity; (1-propylimidazole)-diphenylmethylborane; (1-isopropylimidazole)-diphenylmethylborane; (1-t-butylimidazole)-diphenylmethylborane; (1-cyclopropylimidazole)diphenylmethylborane; (1-2',2',2'-trifluoroethylimidazole)diphenylmethylborane; (1-t-butylimidazole)-diphenylvinylborane; (1-cyclopropylimidazole)-diphenylvinylborane; and (1-vinylimidazole)-diphenylvinylborane. These compounds exhibit excellent preventative activity against a broad spectrum of fungal diseases and especially so the first two compounds.

In terms of manufacturing ease, the compounds wherein X and Y are equal and are located at the same position of the respective phenyl are preferred, i.e., (IA)

(IA)

wherein R, R¹, R², R³ and R⁴ are as defined herein above with respect to formula I and X¹ is hydrogen; alkyl having 1 through 4 carbon atoms; fluoro; chloro; alkoxy having 1 through 4 carbon atoms; alkylthio having 1 through 4 carbon atoms; or haloalkyl having 1 through 4 carbon atoms and 1 through 3 halo substituents independently selected from the group of fluoro, chloro, and bromo; and wherein each of the X¹ groups is located at the same position of the respective phenyl rings to which they are attached.

Definitions

As used herein the following terms have the following meanings unless expressly stated to the contrary:

The term "alkyl" refers to both straight- and branched-chain alkyl groups. The term "lower alkyl" refers to alkyl groups having a total of from 1 through 6 carbon atoms, preferably 1 through 4 carbon atoms and includes primary, secondary and tertiary alkyl groups. Typical lower alkyls include, for example, methyl, ethyl, n-propyl, isopropyl, n-butyl, t-butyl, pentyl, hexyl and the like.

The term "lower alkylene" refers to both straight chained and branched chained alkylene groups having 1 through 6 carbon atoms, preferably 1 through 4 carbon atoms and includes, for example, $$-CH_2; \quad -CH_2-CH_2-; \quad -\underset{\underset{CH_3}{|}}{CH}-CH_2- \text{ and the like.}$$

The term "lower alkenyl" refers to alkenyl groups having 2 through 6, preferably 2 through 4, carbon atoms and includes, for example, vinyl, 1-propenyl, 2-propenyl, 1-methylvinyl, 1-butenyl, 2-methylprop-1-enyl and the like.

The term "lower alkoxy" refers to the group —OR' wherein R' is lower alkyl.

The term "lower alkoxyalkyl" refers to the group R'OR"—wherein R' and R" are independently straight chain or branched chain alkyl groups having 1 through 3 carbon atoms.

The term "lower alkylthio" refers to the group R'S—wherein R' is a straight chain or branched chain alkyl group having 1 through 3 carbon atoms.

The term "halo" refers to the group of fluoro, chloro, bromo and iodo unless expressly defined as referring only to fluoro, chloro and bromo.

The term "aralkyl" refers to the group wherein R' is lower alkyl having 1 through 4 carbon atoms and preferably is methyl or ethyl.

The term "lower haloalkyl" refers to haloalkyl compounds having 1 through 4 carbon atoms and 1 through 3 halo atoms independently selected from the group of fluoro, chloro, bromo. Preferably the lower haloalkyl group has 1 or 2 carbon atoms.

The term "3-substituted alkenyl" refers to the group —CH₂CH=CHY wherein Y is the substituent.

In naming borane complexes the terms "diphenylalkylborane or alkyldiphenylborane" refer to the group wherein R is alkyl.

Similarly, the terms "diphenylalkenylborane, cycloalkyldiphenylborane, diphenylhaloalkyl, and diphenylhaloalkenyl" refer to the group wherein R is the named alkenyl, cycloalkyl, haloalkyl, or haloalkenyl group.

The term "imidazole-diphenylmethylborane" refers to the compound

Since coordination at the N3 nitrogen is presumed in this nomenclature.

The term "room temperature" or "ambient temperature" refers to about 20°–25° C.

The term "compatible salts" refers to salts which do not significantly adversely alter the fungicidal properties or plant safety of the parent compound. Suitable salts include cation salts such as, for example, the cation salts of lithium, sodium, potassium, alkali earth metals, ammonia, quaternary ammonium salts, and the like.

Synthesis

The compounds of Formula I can be prepared by the following schematically represented process:

(1)

(A) + RMgZ ⟶

(B)

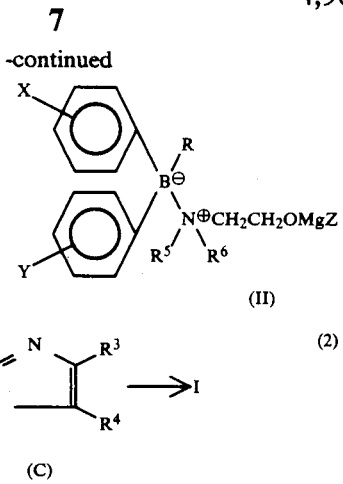

(II)

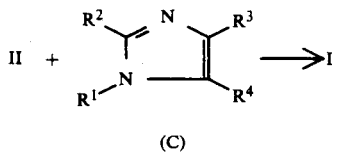

(C)

wherein R, R[1], R[2], R[3], R[4], X and Y are as defined hereinabove, R[5] and R[6] are independently hydrogen or lower alkyl, preferably hydrogen or methyl, and Z is chloride, bromide or iodide.

Step 1 of this process is a Grignard reaction and typically is effected by contacting Compound (A) with the Grignard Reagent (B) under reactive conditions, preferably in an inert organic solvent under substantially anhydrous conditions. Typically, this step is conducted at temperatures in the range of about from 15° C. to 80° C., preferably 20° C. to 35° C., for about from 2 to 24 hours, preferably about from 2 to 4 hours, using about from 1 to 3.5, preferably 1 to 3 moles of Grignard Reagent (B) per mole of Compound (A).

Suitable organic solvents which can be used include, for example, tetrahydrofuran, alkyl ethers (e.g. ethyl ether), hexane, and the like, and compatible mixtures thereof. Best results are obtained using tetrahydrofuran, ethyl ether or glyme as the solvent.

The second step can be effected by contacting intermediate II with imidazole (C), preferably in an inert organic solvent, under reactive conditions. The second step can be conveniently conducted in situ without separation of intermediate II.

Typically, this process is conducted at temperatures in the range of about from 20° C. to 35° C., preferably 20° C. to 25° C., for about from 2 to 24 hours, preferably 10 to 24 hours, using about from 1 to 5, preferably 1 to 3 moles of Compound (C) per mole of Compound (B). Typically, about from 1 to 3 moles of base are used per mole of Compound (C).

Suitable inert organic solvents which can be used include, for example, the solvents listed above with respect to Step 1, and compatible mixtures thereof. Since most conveniently, the second step is conducted in situ, the same solvent will generally be used in the second step as used in the first step.

The starting materials of Formulas (B) and (C) are generally known materials and can be prepared by known procedures, or obvious modifications thereof (i.e., substitution of appropriate starting materials). The preparation of starting materials (A) is, for example, described in Y. Rasiel and H. K. Zimmerman, Ann. 649, 111 (1961) or by R. L. Lestinger and I. Skoog, J. Am. Chem. Soc. 77, 2491 (1955), and in the case where X, Y, R[5] and R[6] are hydrogen, is a commercially available material. The starting materials of Formula B are Grignard Reagents and can be prepared via a standard procedures such as, for example, described in P. E. Pearson, D. Cowan, J. D. Becker, J. Org. Chem. 24, 504 (1959). The starting materials of Formula C are substituted imidazoles can be prepared according to known procedures such as for example described in M. R. Grimmett, *Advance in Heterocyclic Chem.* 12, 103 (1970), Ibid. 27, 241 (1980) and in many instances are commercially available. For example, the 1-substituted imidazoles are either commercially available or can be prepared by alkylating the imidazole sodium salt with the appropriate alkyl halides in dimethylformamide. The 2-substituted imidazoles are either commercially available or can be prepared by the classical Radszizewski reaction with glyoxal, suitable aldehydes, and ammonia in a single step. The 4-(5)-imidazoles are either commercially available or can be prepared by the Weidenhagen reaction of acetoxy ketones with cupric acetate, formaldehyde, and ammonia. Di- or tri-substituted imidazoles can be prepared similarly. The di- or tri-substituted imidazole can be prepared by lithiating and alkylating of mono-substituted imidazoles as described in B. H. Lipshutz, B. Huff, W. Hazen, Tetrahedron Letter 29, 3411 (1988).

The starting materials of Formula A can also be prepared by hydrolysis and oxidation of the corresponding optionally substituted triphenylborane alkali metal hydroxide adduct by procedure of P. Denisevich illustrated hereinbelow in Preparation A. In the case where X and Y are different and/or are not located at the same position of the respective phenyl, the procedure described in D. Giraud et al, *Compte Rendus Hebdomadaires des Sceances de l'Academie des Sciences,* p. 319 v. 254 (1962) can be applied to prepare the compounds of formula I.

The compounds of Formula I also generally can be conveniently prepared via the P. Kenny process using an exchange reaction of an imidazole with a diphenylalkylboron-ammonia complex:

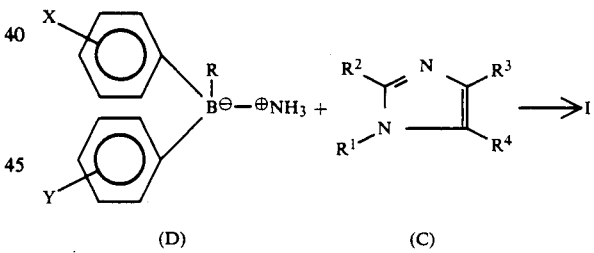

(D)                    (C)

wherein R, R[1], R[2], R[3], R[4], X and Y are defined hereinabove.

In accordance with this process, Compound (D) is contacted with Compound (C) under reactive conditions, preferably in a inert organic solvent under substantially anhydrous conditions.

Preferably, this process is conducted at temperatures in the range of about from 0° C. to reflux, conveniently about 20° C. to 25° C. for about 1 to 72 hours, using about from 0.1 to 1 moles of Compound (C) per mole of Compound (D). Suitable inert organic solvents which can be used include, for example, halogenated alkanes, for example, chloroform, methylene chloride; lower alkenols, for example, methanol, ethanol; acetone and the like and compatible mixtures thereof. The starting material of Formula (D) can be prepared by known procedures such as, for example, described by D. Giraud et al, *Compte Rendus Hebdomadaires des Sceances de l'Academie des Sciences,* p. 319, v. 254 (1962), or by obvious modifications thereof (e.g., use of appropriately substituted reactants and appropriate solvents).

Compound (D) can also be conveniently prepared via the reaction of intermediate II with ammonia.

General Process Conditions

In the above-described processes, the products can be recovered from the respective reaction product mixtures by any suitable separation and purification procedure, such as, for example, extraction, trituration, and recrystallization. Suitable separation and purification procedures are, for example, illustrated in the Examples set forth hereinbelow.

Generally, the reactions described above are conducted as liquid phase reactions and hence pressure is generally not significant except as it affects temperature (boiling point) where reactions are conducted at reflux. Therefore, these reactions are generally conducted at pressures of about from 300 to 3,000 mm of mercury and conveniently are conducted at about atmospheric or ambient pressure.

It should also be appreciated that where typical or preferred process conditions (e.g., reaction temperatures, times, mole ratios of reactants, solvents, pressures, etc.) have been given, that other process conditions could also be used unless otherwise stated. Optimum reaction conditions (e.g., temperature, reaction time, mole ratios, solvents, etc.) may vary with the particular reagents or organic solvents, used but can be determined by routine optimization procedures.

Where optical isomer mixtures are obtained, the respective optical isomers can be obtained by conventional resolution procedures. Geometric isomers and coordination isomers can be separated by conventional separation procedures which depend upon differences in physical properties between the isomers.

Utility

The compounds of the present invention are effective in controlling fungal plant diseases, including downy mildew, leaf blights, leaf spots, damping-off diseases, Botrytis diseases, and post-harvest diseases. Certain of the compounds further exhibit a broad spectrum of activity. The compounds are generally more effective as preventative fungicides and a number of which are especially effective in preventing grey mold (Botrytis), grape downy mildew, late blights in solanaceous crops, and Septoria leaf spot diseases.

The compounds are applied to the subject plants in fungicidally effective amounts. When applied as preventative fungicides, the compounds are preferably applied at prescheduled times prior to the detection of plant infection or immediately upon the detection of infection. The optimum fungicidally effective amount will, of course, depend on several factors such as the host, the type of fungus, weather conditions, and the particular compound of the invention. Generally, however, the compounds are preferably applied at a rate of about from 0.2 to 2.5 kg per hectare for preventative application, and 1 to 3 kg per hectare for eradicant application. The compounds may also be applied for seed treatments. Generally, the compounds are applied as seed treatments at a rate of about 0.5 to 32 g per 100 kg of seeds. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide.

Thus, the fungicides of the invention may be formulated and applied as granules, as powdery dusts, as wettable solutions, as emulsifiable concentrates, as solutions, or as any of several other known types of formulations, depending on the desired mode of application.

Wettable powders are in the form of finely divided particles which disperse readily in water or other dispersant. These compositions normally contain from about 5% to 80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, readily wettable, inorganic diluents. Typical wetting, dispersing or emulsifying agents include, for example: the aryl and alkylaryl sulfonates and their sodium salts; alkylamide sulfonates, including fatty methyl taurides; alkylaryl polyether alcohols, sulfated higher alcohols, and polyvinyl alcohols; polyethylene oxides, sulfonated animal and vegetable oils; sulfonated petroleum oils, fatty acid esters of polyhydric alcohols and the ethylene oxide addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively course particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art. The percentages by weight of the fungicide may vary according to the manner in which the composition is to be applied and the particular type of formulation, but in general comprise 0.05% to 95% of the toxicant by weight of the fungicidal composition, and depending on whether the composition is intended for direct application or dilution prior to application. The compounds are typically applied at rates in the range of about from 0.1 to 5 kg/hectare, preferably 0.2 to 3 kg/hectare, and typically are applied as foliage sprays.

The fungicidal compositions may be formulated and-/or applied with other ingredients, including wetting agents, emulsifiers, adjuvants, stabilizers, etc., as well as other compatible active ingredients such as other fungicides, insecticides, nematocides, bactericides, plant growth regulators, fertilizers, etc.

A further understanding of the invention can be had in the following non-limiting Preparation(s) and Example(s). Wherein, unless expressly stated to the contrary, all temperatures and temperature ranges refer to the Centigrade system and the term "ambient" or "room temperature" refers to about 20°-25° C. The term "percent" or "%" refers to weight percent and the term "mole" or "moles" refers to gram moles. The term "equivalent" refers to a quantity of reagent equal in mole equivalents to the mole equivalent of the preceding or succeeding reactant recited in that example or preparation in terms of finite moles or finite weight or volume. Where given, proton-magnetic resonance spectrum (p.m.r. or n.m.r.) were determined at 90 and 360 mHz, signals are assigned as singlets (s), broad singlets (bs), doublets (d), double doublets (dd), triplets (t), double triplets (dt), quartets (q), and multiplets (m); and cps refers to cycles per second.

PREPARATIONS AND EXAMPLES

PREPARATION A

2-Aminoethyl Diphenyborinate

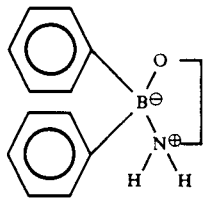

This preparation illustrates the preparation of the title compound via the method of P. Denisevich, Jr.

Aqueous 10 wt % hydrochloric acid is slowly added to 250 g of a solution containing 22.5 g of triphenylborane.sodium hydroxide. The addition of hydrochloric acid is continued until a pH of 1.2. During the addition, cooling is provided to maintain the temperature of the reaction mixture below 30° C. Eighty (80) ml of ethyl ether is added and the mixture stirred overnight (about 10-12 hours) at room temperature during which time a slow steady stream of air is passed through the mixture. Fifty (50) ml of ethyl ether is added to compensate for evaporation losses. The reaction mixture forms a two-phase system. The ethyl ether phase is separated, washed with water and then added to 4.9 g of 2-aminoethanol. The mixture is stirred for one hour at room temperature and then filtered. The recovered solids are washed with water, affording 14.4 g of the title compound m.p. 186°-188° C.

EXAMPLE 1

(1-Isopropylimidazole)-Diphenylmethylborane

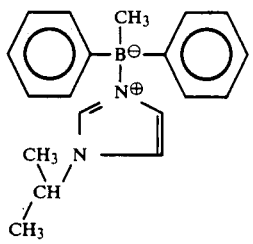

In this example, 2.25 g (0.01 mol) of 2-aminoethyl diphenylborinate is added to 35 mL of ethyl ether at room temperature followed by the dropwise addition of 0.03 mol of methylmagnesium chloride. The mixture is stirred for three hours at room temperature and then 3.3 g (0.03 mol) of isopropylimidazole is added and stirred overnight (12-14 hours) at room temperature. The reaction product mixture is mixed with 100 mL of saturated aqueous ammonium chloride solution and 200 mL of ethyl ether affording a two-phase mixture. The layers are separated and the aqueous layer is combined with the separated ether layer, washed with water, extracted with 100 ml of ethyl ether. The extract is dried over magnesium sulfate, and filtered. The filtrate is evaporated to give a solid which is recrystalized from cold dichloromethane and dried in vacuo to give 2.20 g (76.2% yield) of a white solid, m.p. 180°-182° C.

Similarly, by following the same general procedure using the appropriate starting materials, the following compounds can be prepared:
imidazole-diphenylethylborane;
imidazole-diphenylbutylborane;
imidazole-diphenylisopropylborane;
imidazole-diphenylcyclohexylborane;
(1-methylimidazole)-diphenylmethylborane;
(1-t-butylimidazole)-diphenylethylborane;
(1-octylimidazole)-diphenyl(trifluoromethyl)borane;
(1-decylimidazole)-diphenylethylborane;
(1-dodecylimidazole)-diphenyl(4-chlorobutyl)borane;
[1-(2-ethyl-4,6-dimethyl)heptylimidazole]-diphenylisopropylborane;
(1-cyclopropylimidazole)-diphenylcyclohexylborane;
(1-cyanomethylimidazole)-diphenylmethylborane;
[1-(2-cyanopropyl)imidazole]-diphenylethylborane;
[1-(4-cyanobutyl)imidazole]-diphenylbutylborane;
(1-methoxymethylimidazole-diphenylisopropylborane;
(1-phenylimidazole)-diphenylcyclohexylborane;
[1-(2-phenylethyl)imidazole]-diphenylmethylborane;
[1-(4-bromophenyl)imidazole]-diphenylethylborane;
[1-(2-chlorophenyl)imidazole]-diphenylisopropylborane;
1-(β-hydroxyethylimidazole)-diphenylpropylborane;
[1-(4-cyclohexylphenyl)imidazole-diphenylcyclohexylborane;
[1-(2,6-dimethylphenyl)imidazole-diphenylmethylborane;
[1-(3-propoxycarbonylpropyl)imidazole]-diphenyl(1-chloro-2-fluoroethyl)borane;
[1-(2-chloro-4-fluorophenyl)imidazole]-diphenylethylborane;
[1-(4-fluoro-2-methylphenyl)imidazole-diphenyl(4-bromobutyl)borane;
[1-(3-chloroallyl)imidazole-diphenylisopropylborane;

[1-(2-fluoropent-2-enyl)imidazole]-diphenylcyclohexylborane;
(1-[2-(1,3-dioxolan-2-yl)ethyl]imidazole)-diphenylmethylborane;
(1-[2-(1,3-dioxolan-2-yl)butyl]imidazolediphenyl(1-bromo-2-chloroethyl)borane;
(1-[2-(1,3-dioxolan-2-yl)butyl]imidazole)-diphenylbutylborane;
[1-(2-ethoxypropyl)imidazole]-diphenylisopropylborane;
[1-(2-ethylcarbonylpropyl)imidazole]-diphenylisopropylborane;
[1-(2-chloro-4-nitrobenzyl)imidazole]-diphenylcyclopropylborane;
[1-(4-fluoro-3-methyl-2-nitrobenzyl)imidazole]-diphenyl-t-butylborane;
[1-(3-isopropylpropoxy)imidazole]-diphenylcyclohexylborane;
(2-ethylimidazole)-diphenylmethylborane;
(2-pentylimidazole)-diphenylisopropylborane;
(2-phenylimidazole)-diphenylmethylborane;
(2-benzylimidazole)-diphenylethylborane;
[2-(4-bromobenzyl)imidazole]-diphenylbutylborane;
[2-(3-ethylbenzyl)imidazole]-diphenylisopropylborane;
[2-(2-bromobenzyl)imidazole]-diphenylcyclohexylborane;
[2-(2,6-dimethylbenzyl)imidazole]-diphenylmethylborane;
[2-(2,4-dichlorobenzyl)imidazole]-diphenylethylborane;
[2-(3-fluoro-5-ethylbenzyl)imidazole]-diphenylbutylborane;
[2-(2-chloro-3-iodobenzyl)imidazole]-diphenylcyclohexylborane;
[5-(4-methylpentyl)imidazole]-diphenylmethylborane;
(5-isopropylimidazole)-diphenylethylborane;
(5-t-butylimidazole)-diphenylbutylborane;
(5-ethylimidazole)-diphenylisopropylborane;
(5-methylimidazole)-diphenylcyclohexylborane;
(5-isopropylimidazole)-diphenylmethylborane;
(5-cyclohexylimidazole)-diphenylethylborane;
(5-ethylimidazole)-diphenylbutylborane;
(5-isopropylimidazole)-diphenylisopropylborane;
(5-t-butylimidazole)-diphenylcyclohexylborane;
(5-phenylimidazole)-diphenylmethylborane;
(5-benzylimidazole)-diphenylethylborane;
(5-β-phenethyl)-diphenylbutylborane;
(5-α-phenylpropyl)-diphenylisopropylborane;
imidazole-di(2-methylphenyl)ethylborane;
imidazole-di(3-isopropylphenyl)butylborane;
imidazole-di(4-fluorophenyl)isopropylborane;
(1-methylimidazole)-di(3-ethylphenyl)-t-butylborane;
(1-octylimidazole)di(2-chlorophenyl)methylborane;
(1-dodecylimidazole)di(2-methoxyphenyl)butylborane;
[1-(2-ethyl-4,6-dimethylheptyl)imidazole]-di(4-t-butylthiophenyl)isopropylborane;
(1-cyclopropylimidazole)di(4-1′,1′,2′-trichloroethylphenyl)cyclohexylborane;
(1-cyanomethylimidazole-di(3-trifluoromethylphenyl)methylborane;
[1-(2-cyanopropyl)imidazole]-di(2-methylphenyl)ethylborane;
[1-(4-cyanobutyl)imidazole]-di(3-isopropylphenyl)butylborane;
(1-methoxymethylimidazole)-di(4-fluorophenyl)isopropylborane;
[1-(2-phenylethyl)imidazole]-di(2-chlorophenyl)methylborane;

[1-(4-bromophenyl)imidazole]-di(3-fluorophenyl)ethylborane;
[1-(2-chlorophenyl)imidazole]-di(2-methoxyphenyl)isopropylborane;
[1-(4-cyclohexylphenyl)imidazole]-di(4-t-butylthiophenyl)cyclohexylborane;
[1-(2-chloro-4-fluorophenyl)imidazole]-di(3-trifluoromethylphenyl)ethylborane;
[1-4-fluoro-2-methylphenyl)imidazole]-di(2-methylphenyl)butylborane;
[1-(3-chloroallyl)imidazole]-di(isopropylphenyl)isopropylborane;
[1-(2-fluoropent-2-enyl)imidazole]-di(4-fluorophenyl)cyclohexylborane;
(1-[2-(1,3-dioxolan-2-yl)butyl]imidazole]-di(2-chlorophenyl)ethylborane;
(1-(2-ethoxypropyl)imidazole]-di(2-methoxyphenyl)isopropylborane;
[1-(3-isopropoxypropyl)imidazole]-di(4-butylthiophenyl)cyclohexylborane;
(2-methylimidazole)-di(2-ethoxyphenyl)methylborane;
(2-benzylimidazole)-di(3-trifluoromethylphenyl)ethylborane;
[2-(4-bromobenzyl)imidazole]-di(2-methylphenyl)butylborane;
[2-(3-ethylbenzyl)imidazole]-di(3-isopropylphenyl)isopropylborane;
[2-(2-bromobenzyl)imidazole]-di(4-fluorophenyl)cyclohexylborane;
[2-(2,6-dimethylbenzyl)imidazole]-di(3-chlorophenyl)methylborane;
[2-(2,4-dichlorobenzyl)imidazole]-di(2-chlorophenyl)ethylborane;
[2-(2-chloro-3-iodobenzyl)imidazole]-di(2-methoxyphenyl)cyclohexylborane;
[5-(4-methylpentyl)imidazole]-di(4-t-butylthiophenyl)methylborane;
(5-t-butylimidazole)-di(2-methylphenyl)butylborane;
(5-ethylimidazole)-di(3-trifluoromethylphenyl)ethylborane;
(5-methylimidazole)-di(3-isopropylphenyl)cyclohexylborane;
(5-isopropylimidazole-di(4-fluorophenyl)methylborane;
(5-isopropylimidazole)-di(3-chlorophenyl)isopropylborane;
(5-t-butylimidazole)-di(2-methoxyphenyl)cyclohexylborane;
(5-phenylimidazole)-di(3-fluorophenyl)ethylborane;
(5-2′-phenylpropylimidazole)-di(3-ethoxyphenyl)borane;
(1-methyl-2-phenylimidazole)-diphenylmethylborane;
(2-ethyl-1-t-butylimidazole)-diphenylethylborane;
(2-benzyl-1-octylimidazole)-diphenylmethylborane;
(2-4′-chlorobenzyl-1-decylimidazole)-diphenylethylborane;
(1-dodecyl-2-p-fluorobenzylimidazole)-diphenylbutylborane;
[1-(2-ethyl-4,6-dimethyl)-2-(2-chloro-4-fluorobenzyl)-heptylimidazole]diphenylisopropylborane;
(1-cyclopropyl-2-2′-methylbenzylimidazole)-diphenylcyclohexylborane;
(1-cyanomethyl-2-3′-hexylbenzylimidazole)-diphenylmethylborane;
[1-(2-cyanopropyl)-2-(2,6-dimethylbenzyl)imidazole]diphenylethylborane;
[1-(4-cyanobutyl)imidazole-2-(2-chloro-4-fluorobenzyl)]diphenylbutylborane;
(1-methoxymethylimidazole)-diphenylisopropylborane;

(1-phenyl-2-p-bromobenzylimidazole)-diphenylcyclohexylborane;
[2-(2-iodobenzyl)-1-(2-phenylethyl)imidazole]-diphenylmethylborane;
[1-(4-bromophenyl)imidazole]-diphenylethylborane;
[1-(2-chlorophenyl)imidazole]-diphenylisopropylborane;
(1-β-hydroxyethyl-5-methylimidazole)-diphenylpropylborane;
[1-(4-cyclohexylphenyl)-5-butylimidazole]-diphenylcyclohexylborane;
[5-benzyl-1-(2,6-dimethylphenyl)imidazole]-diphenylmethylborane;
[1-(2-chloro-4-fluorophenyl)-5-isopropylimidazole]-diphenylethylborane;
[1-(4-fluoro-2-methylphenyl)-5-phenylimidazole]-diphenylbutylborane;
[1-(3-chloroallyl)-5-β-phenylethylimidazole]-diphenylisopropylborane;
[1-(2-fluoropent-2-enyl)-5-(2-phenylpentyl)imidazole]-diphenylcyclohexylborane;
(5-butyl-1-[2-(1,3-dioxolan-2-yl)ethyl]imidazole)-diphenylmethylborane;
(1-[2-(1,3-dioxolan-2-yl)butyl]-5-methylimidazole)-diphenylethylborane;
(1-[2-(1,3-dioxolan-2-yl)butyl]-5-phenylimidazole)-diphenylbutylborane;
[1-(2-ethoxypropyl)-5-isopropylimidazole]-diphenylisopropylborane;
[1-(3-isopropoxypropyl)-5-phenylimidazole]-diphenylcyclohexylborane;
(5-butyl-2-ethylimidazole)-diphenylmethylborane;
(5-methyl-2-pentylimidazole)-diphenylisopropylborane;
(2-phenyl-5-phenylimidazole)-diphenylmethylborane;
(2-benzylimidazole)-diphenylethylborane;
[2-(4-bromobenzyl)-5-(2-phenylbutyl)imidazole]-diphenylbutylborane;
[2-(3-ethylbenzyl)-5-isopropylimidazole]-diphenylisopropylborane;
[2-(2-bromobenzyl)-5-hexylimidazole]-diphenylcyclohexylborane;
[2-(2,6-dimethylbenzyl)-5-methylimidazole]-diphenylmethylborane;
[2-(2,4-dichlorobenzyl)-5-t-butylimidazole]-diphenylethylborane;
[5-benzyl-2-(3-fluoro-5-ethylbenzyl)imidazole]-diphenylbutylborane;
[2-(2-chloro-3-iodobenzyl)imidazole]-diphenylcyclohexylborane;
[4,5-dimethylimidazole]-diphenylmethylborane;
[4,5-di-(t-butyl)imidazole]-diphenylethylborane;
(4,5-diethylimidazole)-diphenylbutylborane;
(4,5-dipentylimidazole)-diphenylisopropylborane;
(5-methylimidazole)-diphenylcyclohexylborane;
[4,5-di(isopropyl)imidazole]-diphenylmethylborane;
(4,5-diethylimidazole)-diphenylbutylborane;
(4,5-dipentylimidazole)-diphenylisopropylborane;
(4,5-dipentylimidazole)-diphenylcyclohexylborane;
(4-methyl-4,5-dihexylimidazole)-diphenylmethylborane;
[4,5-di(sec-butyl)-pentylimidazole]-diphenylethylborane;
[4,5-(isopropyl)-imidazole]-diphenylbutylborane;
(4,5-diethylimidazole)-diphenylisopropylborane;
(1,2-methylimidazole)-di(3-ethylphenyl)-t-butylborane;
(5-methyl-1-octylimidazole)-di(2-chlorophenyl)methylborane;
(1-dodecyl-5-phenylimidazole)-di(2-methoxyphenyl)butylborane;
[1-(2-ethyl-4,6-dimethylheptyl)-5-propylimidazole]-di(4-t-butylthiophenyl)isopropylborane;
(1-cyclopropyl-5-3'hexylimidazole)-di(4-1',1',2'-trichloroethylphenyl)cyclohexylborane;
(1-cyanomethyl-2-phenylimidazole)-di(3-trifluoromethylphenyl)methylborane;
[1-(2-cyanopropyl)-5-phenylimidazole]-di(2-methylphenyl)ethylborane;
[1-(4-cyanobutyl)-2-p-fluorophenylimidazole]-di(3-isopropylphenyl)butylborane;
(1-methoxymethyl-2-σ-methylimidazole)-di(4-fluorophenyl)isopropylborane;
[1-(2-phenylethyl)-5-(3-phenylpentyl)imidazole]-di(2-chlorophenyl)methylborane;
[1-(4-bromophenyl)-5-methylimidazole]-di(2-fluorophenyl)ethylborane;
[1-(2-chlorophenyl)-5-isopropylimidazole]-di(2-methoxyphenyl)isopropylborane;
[1-(4-cyclohexylphenyl)-5-benzylimidazole]-di(4-t-butylthiophenyl)cyclohexylborane;
[1-(2-chloro-4-fluorophenyl)-5-methylimidazole]-di(3-trifluoromethylphenyl)ethylborane;
[1-(4-fluoro-2-methylphenyl)-5-isopropylimidazole]-di(2-methylphenyl)butylborane;
[1-(3-chloroallyl)-5-ethylimidazole]-di(isopropylphenyl)isopropylborane;
[1-(2-fluoropent-2-enyl)-5-phenylimidazole]-di(4-fluorophenyl)cyclohexylborane;
(1-[2-(1,3-dioxolan-2-yl)butyl]-5-phenylimidazole)-di(2-chlorophenyl)ethylborane;
[1-(2-ethoxypropyl)-5-β-phenylethylimidazole]-di(2-methoxyphenyl)isopropylborane;
[1-(3-isopropoxypropyl)-5-methylimidazole]-di(4-butylthiophenyl)cyclohexylborane;
(1,2-dimethylimidazole)-di(2-ethoxyphenyl)methylborane;
(2-benzyl-1-methylimidazole)-di(3-trifluoromethylphenyl)ethylborane;
[2-(4-bromobenzyl)-5-phenylimidazole]-di(2-methylphenyl)butylborane;
[2-(3-ethylbenzyl)-5-methylimidazole]-di(3-isopropylphenyl)isopropylborane;
[2-(2-bromobenzyl)-5-isopropylimidazole]-di(4-fluorophenyl)cyclohexylborane;
[5-benzyl-2-(2,6-dimethylbenzyl)imidazole]-di(3-chlorophenyl)methylborane;
[1-methyl-2-(2,4-dichlorobenzyl)imidazole]-di(2-chlorophenyl)ethylborane;
[4,5-di(t-butyl)imidazole]-di(2-methylphenyl)butylborane;
(4,5-diethylimidazole)-di(3-trifluoromethylphenyl)ethylborane;
(4,5-dimethylimidazole)-di(3-isopropylphenyl)cyclohexylborane;
(4,5-dipentylimidazole)-di(4-fluorophenyl)methylborane;
[4,5-di(isopropyl)imidazole]-di(2-chlorophenyl)isopropylborane;
[4,5-di(t-butyl)imidazole]-di(2-methoxyphenyl)cyclohexylborane;
(4,5-dihexylimidazole)-di(3-fluorophenyl)ethylborane;
(4-butyl-5-2'-phenylpropylimidazole)-di(3-ethoxyphenyl)borane;
imidazole-phenyl(σ-tolyl)methylborane;
imidazole-(4-fluorophenyl)phenylethylborane;
imidazole-diphenylbutylborane;

imidazole-(2-chlorophenyl)phenylisopropylborane;
imidazole-(3-methoxyphenyl)phenylcyclohexylborane;
(1-methylimidazole)-(2-ethylthiophenyl)phenylmethylborane;
(1-t-butylimidazole)-(4-trifluoromethylphenyl)phenylethylborane;
(1-octylimidazole)-(3-isopropylphenyl)phenylmethylborane;
(1-decylimidazole)-(3-fluorophenyl)phenylethylborane;
(1-dodecylimidazole)-(phenyl)(2-propoxyphenyl)butylborane;
[1-(2-ethyl-4,6-dimethyl)heptylimidazole]-(4-butylphenyl)phenylisopropylborane;
(1-cyclopropylimidazole)-(4-1',2',2'-trichlorophenyl)-phenylcyclohexylborane;
(1-methoxymethylimidazole-phenyl-(2-isopropoxyphenyl)isopropylborane;
(1-phenylimidazole)-phenyl(3-methylthiophenyl)cyclohexylborane;
[1-(2-phenylethyl)imidazole]-(3-4'-bromobutylphenyl)-phenylmethylborane;
[1-(4-bromophenyl)imidazole]-phenyl(4-propylphenyl)ethylborane;
1-(β-hydroxyethylimidazole)-phenyl(2-methoxyphenyl)propylborane;
[1-(4-cyclohexylphenyl)imidazole-(2-t-butylthiophenyl)phenylcyclohexylborane;
[1-(2,6-dimethylphenyl)imidazole-(3-chloromethylphenyl)phenylmethylborane;
[1-(3-propoxycarbonylpropyl)imidazole]-phenyl(p-tolyl)ethylborane;
[1-(4-fluoro-2-methylphenyl)imidazole-(2-ethoxyphenyl)phenylbutylborane;
[1-(3-chloroallyl)imidazole-phenyl(2-propylthiophenyl)isopropylborane;
[1-(2-fluoropent-2-enyl)imidazole]-phenyl(2-trifluoromethylphenyl)cyclohexylborane;
(1-[2-(1,3-dioxolan-2-yl)ethyl]imidazole)-(2-fluorophenyl)phenylmethylborane;
[1-(2-ethoxypropyl)imidazole]-(2-bromomethylphenyl)-phenylisopropylborane;
[1-(2-ethylcarbonylpropyl)imidazole]-(3-isopropylphenyl)phenylisopropylborane;
[1-(2-chloro-4-nitrobenzyl)imidazole]-(4-methoxyphenyl)phenylcyclopropylborane;
[1-(4-fluoro-3-methyl-2-nitrobenzyl)imidazole]-(2-isopropylthiophenyl)phenyl-t-butylborane;
[1-(3-isopropoxypropyl)imidazole]-phenyl(σ-tolyl)cyclohexylborane;
(2-ethylimidazole)-(2-methoxyphenyl)phenylmethylborane;
(2-phenylimidazole)-(3-ethylthiophenyl)phenylmethylborane;
(2-benzylimidazole)-diphenylethylborane;
[2-(4-bromobenzyl)imidazole]-phenyl(2-trifluoromethylphenyl)butylborane;
[2-(3-ethylbenzyl)imidazole]-(3-ethylphenyl)phenylisopropylborane;
[2-(2,6-dimethylbenzyl)imidazole]-phenyl(tolyl)methylborane;
[2-(3-fluoro-5-ethylbenzyl)imidazole]-(3-ethoxylphenyl)phenylbutylborane;
[5-(4-methylpentyl)imidazole]-phenyl(p-tolyl)methylborane;
(5-isopropylimidazole)-(3-chlorophenyl)phenylethylborane;
(5-t-butylimidazole)-(2-isopropoxyphenyl)phenylbutylborane;
(5-cyolohexylimidazole)-(4-isopropylthiophenyl)-phenylethylborane;
(5-phenylimidazole)-(3-2'-bromo-3'-chloropropylphenyl)phenylmethylborane;
(5-benzylimidazole)-phenyl(m-tolyl)ethylborane;
(5-β-phenethyl)-(3-butoxyphenyl)phenylbutylborane;
imidazole-(2-methylphenyl)(p-tolyl)ethylborane;
imidazole-(4-fluorophenyl)(2-methoxylphenyl)isopropylborane;
(1-methylimidazole)-(3-ethylphenyl)(2-fluorophenyl)-t-butylborane;
(1-octylimidazole)(2-chlorophenyl)(4-ethylthiophenyl)methylborane;
(1-dodecylimidazole)(2-methoxyphenyl)(3-t-butylphenyl)butylborane;
[1-(2-ethyl-4,6-dimethylheptyl)imidazole]-(3-t-butylphenyl)(4-t-butylthiophenyl)isopropylborane;
(1-cyclopropylimidazole)(p-tolyl)(4-1',1',2'-trichloroethylphenyl)cyclohexylborane;
(1-cyanomethylimidazole-(3-trifluoromethylphenyl)(4-trifluoromethylphenyl)methylborane;
(1-methoxymethylimidazole)-(4-fluorophenyl)(2-chlorophenyl)isopropylborane;
[1-(2-phenylethyl)imidazole]-(2-chlorophenyl)methylborane;
[1-(4-bromophenyl)imidazole]-(2-bromomethylphenyl)(3-methoxyphenyl)ethylborane;
[1-(2-chlorophenyl)imidazole]-di(2-methoxyphenyl)isopropylborane;
[1-(4-cyclohexylphenyl)imidazole]-(4-t-butylthiophenyl)(4-methoxyphenylcyclohexylborane;
(5-t-butylimidazole)-(2-methylphenyl)(3-fluorophenyl)-butylborane;
(5-ethylimidazole)-(2-methylthiophenyl)(3-trifluoromethylphenyl)ethylborane;
(5-phenylimidazole)-(3-fluorophenyl)(3-ethylphenyl)ethylborane;
(5-2'-phenylpropylimidazole)-di(3-ethoxyphenyl)trifluoromethylborane;
(1-methyl-2-phenylimidazole)-diphenyl(2,2-dichloroethyl)borane;
[1-(2-ethyl-4,6-dimethyl)-2-(2-chloro-4-fluorobenzyl)-heptylimidazole]-phenyl(σ-tolyl)isopropylborane;
(1-cyclopropyl-2-2'-methylbenzylimidazole)-(4-fluorophenyl)phenylcyclohexylborane;
[1-(2-cyanopropyl)-2-(2,6-dimethylbenzyl)imidazole](3-methoxyphenyl)phenylethylborane;
(5-butyl-2-ethylimidazole)-phenyl(p-tolyl)methylborane;
[4-methyl-5-(4-methylpentyl)imidazole]-(2-ethoxyphenyl)phenylmethylborane;
(5-cyclohexyl-4-methylimidazole)-(3-chlorophenyl)-phenylethylborane;
(1,2-methylimidazole)-(3-ethylphenyl)(4-propoxyphenyl)-t-butylborane;
(5-methyl-1-octylimidazole)-(2-chlorophenyl)(3-trifluoromethylphenyl)methylborane;
(1-dodecyl-5-phenylimidazole)-(2-methoxyphenyl)(2-ethylthiophenyl)butylborane;
[1-(2-ethyl-4,6-dimethylheptyl)-5-propylimidazole](4-t-butylthiophenyl)(2-ethylphenyl)isopropylborane;
[4,5-di(isopropyl)imidazole]-(2-chlorophenyl)(4-propylthiophenyl)isopropylborane; and
(5-t-butyl-4-isopropylimidazole)-(2-methoxyphenyl)(2-chlorophenyl)cyclohexylborane.

EXAMPLE 2

(1-Vinylimidazole) Diphenylvinylboron

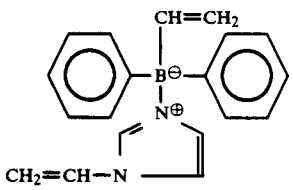

In this example, 2.25 g (0.01 mol) of 2-aminoethyl diphenylborinate is dissolved in 30 ml of tetrahydrofuran at room temperature followed by the dropwise addition of 0.03 mol of vinylmagnesium bromide over a fifteen-minute period. The mixture is stirred for two hours at room temperature and then 0.01 mol of 1-vinylimidazole is added. The mixture is stirred for about 18 hours at room temperature and then quenched by the addition of 40 ml of aqueous 5% hydrochloric acid. The mixture is extracted twice with 40 ml of ethyl ether. The extracts are combined, washed with water and saturated aqueous sodium chloride solution, then dried over magnesium sulfate, filtered, and evaporated to dryness, affording a tan solid. The solid is washed with 60 ml of cold ethyl ether and 60 ml of hexane, and dried in vacuo affording 2.25 g of the title compound as a white powdery solid, m.p. 160°–161° C.

Similarly, by following the same general procedure using the appropriate starting materials, the following compounds can be prepared:

imidazole-diphenylallylborane;
imidazole-diphenyl(2-methylbut-4-enyl)borane;
imidazole-diphenyl(5,5,5-trifluoropent-3-enyl)borane;
imidazole-diphenyl(4-chloro-5-fluorohex-2-enyl)borane;
(1-octylimidazole)-diphenylvinylborane;
(1-decylimidazole)-diphenylallylborane;
(1-dodecylimidazole)-diphenyl(2-methylbut-4-enyl)borane;
(1-hydroxymethylimidazole)-diphenylvinylborane;
[1-(2-ethyl-4,6-dimethylheptyl)imidazole]-diphenyl(5,5,5-trifluoropent-3-enyl)borane;
(1-cyclopropylimidazole)-diphenyl(4-chloro-5-fluorohex-2-enyl)borane;
(1-cyanomethylimidazole)-diphenylvinylborane;
[1-(2-cyanopropyl)imidazole]-diphenylallylborane;
[1-(4-cyanobutyl)imidazole]-diphenyl(2-methylbut-4-enyl)borane;
(1-methoxymethylimidazole)-diphenyl(5,5,5-trifluoropent-3-enyl)borane;
(1-phenylimidazole)-diphenyl(4-chloro-5-fluorohex-2-enyl)borane;
[1-(2-phenylethyl)imidazole]-diphenylvinylborane;
[1-(4-bromophenyl)imidazole]-diphenylallylborane;
[1-(2-chlorophenyl)imidazole]-diphenyl(2-methylbut-4-enyl)borane;
[1-(4-hexylphenyl)imidazole]-diphenyl(5,5,5-trifluoropent-3-enyl)borane;
[1-(2,6-dimethylphenyl)imidazole]-diphenyl(4-chloro-5-fluorohex-2-enyl)borane;
[1-(2-chloro-4-fluorophenyl)imidazole]-diphenylvinylborane;
[1-(4-fluoro-2-methylphenyl)imidazole]-diphenylallylborane;
[1-(3-chloroallyl)imidazole]-diphenyl(2-methylbut-4-enyl)borane;
[1-(2-fluoropent-2-enyl)imidazole]-diphenyl(5,5,5-trifluoropent-3-enyl)borane;
(1-[2-(1,3-dioxolan-2-yl)ethyl]imidazole)-diphenyl(4-chloro-5-fluorohex-2-enyl)borane;
(1-[2-(1,3-dioxolan-2-yl)butyl]imidazole)-diphenylvinylborane;
(1-[2-(1,3-dioxolan-2-yl)butyl]imidazole)-diphenylallylborane;
[1-(2-ethoxypropyl)imidazole]-diphenyl(2-methylbut-4-enyl)borane;
[1-(3-isopropyxoyropyl)imidazole]-diphenyl(5,5,5-trifluoropent-3-enyl)borane;
[1-(2-phenylethyl)imidazole]-diphenylvinylborane;
(2-benzylimidazole)-diphenylvinylborane;
[2-(4-bromobenzyl)imidazole]-diphenylallylborane;
[2-(4-ethylbenzy)imidazole]-diphenyl(2-methylbut-4-enyl)borane;
[2-(2-bromobenzyl)imidazole]-diphenyl(5,5,5-trifluoropent-3-enyl)borane;
[2-(2,6-dimethylbenzyl)imidazole]-diphenyl(4-chloro-5-fluorohex-2-enyl)borane;
[2-(2,4-dichlorobenzyl)imidazole]-diphenylvinylborane;
[2-(3-fluoro-5-ethylbenzyl)imidazole]-diphenylallylborane;
[2-(2-chloro-3-iodobenzyl)imidazole]-diphenyl(2-methylbut-4-enyl)borane;
[5-(4-methylpentyl)imidazole]-diphenyl(5,5,5-trifluoropent-3-enyl)borane;
(5-isopropylimidazole)-diphenyl(4-chloro-5-fluorohex-2-enylborane;
(5-t-butylimidazole)-diphenylvinylborane;
(5-ethylimidazole)-diphenylallylborane;
(5-methylimidazole)-diphenyl(2-methylbut-4-enyl)borane;
(5-isopropylimidazole)-diphenyl(5,5,5-trifluoropent-3-enyl)borane;
(5-hexylimidazole)-diphenyl(4-chloro-5-fluorohex-2-enyl)borane;
(5-ethylimidazole)-diphenylvinylborane;
(5-isopropylimidazole)-diphenylallylborane;
(5-t-butylimidazole)-diphenyl(2-methylbut-4-enyl)borane;
imidazole-di(2-methylphenyl)allylborane;
imidazole-di(3-isopropylphenyl)(2-methylbut-4-enyl)borane;
imidazole-di(4-fluorophenyl)(5,5,5-trifluoropent-3-enyl)borane;
imidazole-di(3-chlorophenyl)(4-chloro-5-fluorohex-2-enyl)borane;
(1-octylimidazole)-di(2-chlorophenyl)vinylborane;
(1-decylimidazole)-di(2-fluorophenyl)allylborane;
(1-dodecylimidazole)-di(2-methoxyphenyl)(2-methylbut-4-enyl)borane;
(1-ethyl-4,6-dimethylheptylimidazole)-di(2-t-butylthiophenyl)(5,5,5-trifluoropent-3-enyl)borane;
(1-cyclopropylimidazole)-di(4-1′,1′,2′,2′-tetrachloroethylphenyl)(4-chloro-5-fluorohex-2-enyl)borane;
(1-cyanomethylimidazole)-di(3-trifluoromethylphenyl)vinylborane;
[1-(2-cyanopropyl)imidazole]-di(2-methylphenyl)allylborane;
[1-(4-cyanobutyl)imidazole]-di(3-isopropylphenyl)(2-methylbut-4-enyl)borane;
(1-methoxymethylimidazole)-di(4-fluorophenyl)(5,5,5-trifluoropent-3-enyl)borane;

(1-phenylimidazole)-di(3-chlorophenyl)(4-chloro-5-fluorohex-2-enyl)borane;
[1-(2-phenylethyl)imidazole]-di(2-chlorophenyl)vinylborane;
[1-(2-chlorophenyl)imidazole]-di(2-methoxyphenyl)(2-methylbut-4-enyl)borane;
[1-(4-hexylphenyl)imidazole]-di(4-t-butylthiophenyl)(5,5,5-trifluoropent-3-enyl)borane;
[1-(2-chloro-4-fluorophenyl)imidazole]-di(3-trifluoromethylphenyl)vinylborane;
[1-(1-fluoro-2-methylphenyl)imidazole]-di(2-methylphenyl)allylborane;
[1-(3-chloroallyl)imidazole]-di(3-isopropylphenyl)(2-methylbut-4-enyl)borane;
[1-(2-fluoropent-2-enyl)imidazole]-di(4-fluorophenyl)(5,5,5-trifluoropent-3-enyl)borane;
(1-[2-(1,3-dioxolan-2-yl)butyl]imidazole)-di(2-chlorophenyl)vinylborane;
[1-(2-ethoxypropyl)imidazole]-di(2-methoxyphenyl)(2-methylbut-4-enyl)borane;
[1-(3-isopropylpropoxy)imidazole]-di(4-t-butylthiophenyl)(5,5,5-trifluoropent-3-enyl)borane;
(2-benzylimidazole)-di(3-trifluoromethylphenyl)vinylborane;
[2-(4-bromobenzyl)imidazole]-di(2-methylphenyl)allylborane;
[2-(3-ethylbenzyl)imidazole]-di(3-isopropylphenyl)(2-methylbut-4-enyl)borane;
[2-(2-bromobenzyl)imidazole]-di(4-fluorophenyl)(5,5,5-trifluoropent-3-enyl)borane;
[2-(2,4-dichlorobenzyl)imidazole]-di(2-chlorophenyl)ethylborane;
[2-(3-fluoro-5-ethylbenzyl)imidazole]-di(2-fluorophenyl)butylborane;
[2-(2-chloro-3-iodobenzyl)imidazole]-di(2-methoxyphenyl)(2-methylbut-4-enyl)borane;
[5-(4-methylpentyl)imidazole]-di(4-t-butylthiophenyl)5,5,5-trifluoropent-3-enyl)borane;
(5-t-butylimidazole)-di(3-trifluoromethylphenyl)vinylborane;
(5-ethylimidazole)-di(2-methylphenyl)allylborane;
(5-methylimidazole)-di(3-isopropylphenyl)(2-methylbut-4-enyl)borane;
(5-isopropylimidazole)-di(4-fluorophenyl)(5,5,5-trifluoropent-3-enyl)borane;
(5-hexylimidazole)-di(3-iodophenyl)(4-chloro-5-fluorohex-2-enyl)borane;
(5-ethylimidazole)-di(2-chlorophenyl)vinylborane;
(5-t-butylimidazole)-di(2-methoxyphenyl)(2-methylbut-4-enyl)borane;
(1,2-dimethylimidazole)-diphenylvinylborane;
(1-isopropyl-2-methylimidazole)-diphenylvinylborane;
(2-butyl-1-octylimidazole)-diphenylvinylborane;
(1-decyl-2-phenylimidazole)-diphenylallylborane;
(2-benzyl-1-dodecylimidazole)-diphenyl(2-methylbut-4-enyl)borane;
(1-hydroxymethyl-p-fluorobenzylimidazole)-diphenylvinylborane;
[1-(2-chloro-4-fluorobenzyl)-1-(2-ethyl-4,6-dimethylheptyl)imidazole]-diphenyl(5,5,5-trifluoropent-3-enyl)borane;
[1-cyclopropyl(2,6-dimethylbenzyl)imidazole]-diphenyl(4-chloro-5-fluorohex-2-enyl)borane;
(1-cyanomethyl-5-methylimidazole)-diphenylvinylborane;
[1-(2-cyanopropyl)-5-propylimidazole]-diphenylallylborane;
[1-(4-cyanobutyl)-5-isopropylimidazole]-diphenyl(2-methylbut-4-enyl)borane;
(5-butyl-1-methoxymethylimidazole)-diphenyl(5,5,5-trifluoropent-3-enyl)borane;
(1,5-diphenylimidazole)-diphenyl(4-chloro-5-fluorohex-2-enyl)borane;
[5-ethyl-1-(2-phenylethyl)imidazole]-diphenylvinylborane;
[1-(4-bromophenyl)-5-isopropylimidazole]-diphenylallylborane;
[1-(2-chlorophenyl)imidazole]-diphenyl(2-methylbut-4-enyl)borane;
[1-(4-hexylphenyl)-5-β-phenylethylimidazole]-diphenyl(5,5,5-trifluoropent-3-enyl)borane;
[1-(2,6-dimethylphenyl)-5-methylimidazole]-diphenyl(4-chloro-5-fluorohex-2-enyl)borane;
[1-(2-chloro-4-fluorophenyl)-5-phenylimidazole]-diphenylvinylborane;
[1-(4-fluoro-2-methylphenyl)imidazole]-diphenylallylborane;
[1-(3-chloroallyl)-5-isopropylimidazole]-diphenyl(2-methylbut-4-enyl)borane;
[1-(2-fluoropent-2-enyl)imidazole]-diphenyl(5,5,5-trifluoropent-3-enyl)borane;
(1-[2-(1,3-dioxolan-2-yl)ethyl]-5-methylimidazole)-diphenyl(4-chloro-5-fluorohex-2-enyl)borane;
(1-[2-(1,3-dioxolan-2-yl)butyl]-2-methylimidazole)-diphenylvinylborane;
(1-[2-(1,3-dioxolan-2-yl)butyl]-5-phenylimidazole)-diphenylallylborane;
[1-(2-ethoxypropyl)imidazole]-diphenyl(2-methylbut-4-enyl)borane;
[5-ethyl-1-(3-isoproprypropyl)imidazole]-diphenyl(5,5,5-trifluoropent-3-enyl)borane;
[5-benzyl-1-(2-phenylethyl)imidazole]-diphenylvinylborane;
(2-benzyl-5-methylimidazole)-diphenylvinylborane;
[2-(4-bromobenzyl)-5-propylimidazole]-diphenylallylborane;
[2-ethylbenzyl-5-(3-pentyl)imidazole]-diphenyl(2-methylbut-4-enyl)borane;
[2-(2-bromobenzyl)-5-phenylimidazole]-diphenyl(5,5,5-trifluoropent-3-enyl)borane;
[2-(2,6-dimethylbenzyl)-5-isopropylimidazole]-diphenyl(4-chloro-5-fluorohex-2-enyl)borane;
[2-(2,4-dichlorobenzyl)-5-(2,2-dimethylbutyl)imidazole]diphenylvinylborane;
[2-(3-fluoro-5-ethylbenzyl)-5-phenylimidazole]-diphenylallylborane;
[5-benzyl-2-(2-chloro-3-iodobenzyl)imidazole]-diphenyl(2-methylbut-4-enyl)borane;
[4,5-diethylimidazole]-diphenyl(5,5,5-trifluoropent-3-enyl)borane;
(4,5-dimethylimidazole)-diphenyl(4-chloro-5-fluorohex-2-enyl)borane;
(4,5-diisopropylimidazole)-diphenylvinylborane;
(4,5-dipentylimidazole)-diphenylallylborane;
(4,5-dibutylimidazole)-diphenyl(2-methylbut-4-enyl)borane;
(4,5-dimethylimidazole)-diphenyl(5,5,5-trifluoropent-3-enyl)borane;
[4,5-di(3,3-dimethylbutyl)imidazole]-diphenyl(4-chloro-5-fluorohex-2-enyl)borane;
(4,5-diethylimidazole)-diphenylvinylborane;
(5-isopropylimidazole)-diphenylallylborane;
(4,5-dihexylimidazole)-diphenyl(2-methylbut-4-enyl)borane;
(4,5-dimethylimidazole)-diphenylvinylborane;

(4,5-diisopropylimidazole)-diphenylallylborane;
(1-octyl-5-methylimidazole)-di(2-chlorophenyl)vinylborane;
(1-decyl-5-methylimidazole)-di(2-fluorophenyl)allylborane;
(1-dodecyl-5-methylimidazole)-di(2-methoxyphenyl)(2-methylbut-4-enyl)borane;
(1-ethyl-4,6-dimethylheptyl-5-methylimidazole)-di(2-t-butylthiophenyl)5,5,5-trifluoropent-3-enyl)borane;
(1-cyclopropyl-5-methylimidazole)-di(4-1',1',2',2'-tetrachloroethylphenyl)(4-chloro-5-fluorohex-2-enyl)borane;
(1-cyanomethyl-5-methylimidazole)-di(3-trifluoromethylphenyl)vinylborane;
[1-(2-cyanopropyl)-5-methylimidazole]-di(2-methylphenyl)allylborane;
[1-(4-cyanobutyl)-5-phenylimidazole]-di(3-isopropylphenyl)(2-methylbut-4-enyl)borane;
(1-methoxymethyl-5-phenylimidazole)-di(4-fluorophenyl)(5,5,5-trifluoropent-3-enyl)borane;
(1-phenyl-5-phenylimidazole)-di(3-chlorophenyl)(4-chloro-5-fluorohex-2-enyl)borane;
[1-(2-phenylethyl-5-phenylimidazole)-di(2-chlorophenyl)vinylborane;
[1-(2-chlorophenyl)-2-methylimidazole]-di(2-methoxyphenyl)(2-methylbut-4-enyl)borane;
[1-(4-hexylphenyl)-2-methylimidazole]-di(4-t-butylthiophenyl)(5,5,5-trifluoropent-3-enyl)borane;
[1-(2-chloro-4-fluorophenyl)-2-phenylimidazole]-di(3-trifluoromethylphenyl)vinylborane;
[1-(1-fluoro-2-methylphenyl)-2-phenylimidazole]-di(2-methylphenyl)allylborane;
[1-(3-chloroallyl)-2-phenylimidazole]-di(3-isopropylphenyl)(2-methylbut-4-enyl)borane;
[1-(2-fluoropent-2-enyl)-2-phenylimidazole]-di(4-fluorophenyl)(5,5,5-trifluoropent-3-enyl)borane;
(1-[2-(1,3-dioxolan-2-yl)butyl]-2-phenylimidazole)-di(2-chlorophenyl)vinylborane;
[5-benzyl-1-(2-ethoxypropyl)imidazole]-di(2-methoxyphenyl)(2-methylbut-4-enyl(borane;
[2-(2-bromo-3-chlorobenzyl)-1-(3-isopropylpropoxy)imidazole]di(4-t-butylthiophenyl)(5,5,5-trifluoro-3-enyl)borane;
(2-benzyl-5-methylimidazole)-di(3-trifluoromethylphenyl)vinylborane;
[2-(4-bromobenzyl)-5-phenylimidazole]-di(2-methylphenyl)allylborane;
[2-(3-ethylbenzyl)-5-α-phenylpropylimidazole]-di(3-isopropylphenyl)(2-methylbut-4-enyl)borane;
[2-(2-bromobenzyl)-5-isopropylimidazole[-di(4-fluorophenyl)(5,5,5-trifluoropent-3-enyl)boran;
[2-(2,4-dichlorobenzyl)-5-ethylimidazole]-di(2-chlorophenyl)ethylborane;
[2-(3-fluoro-5-ethylbenzyl)-5-isopropylimidazole]-di(2-fluorophenyl)butylborane;
[2-(2-chloro-3-iodobenzyl)-5-phenylimidazole]-di(2-methoxyphenyl)(2-methylbut-4-enyl)borane;
[4-ethyl-5-(4-methylpentyl)imidazole]-di(4-t-butylthiophenyl)(5,5,5-trifluoropent-3-enyl)borane;
[(4,5-di(t-butyl)imidazole)-di(3-trifluoromethylphenyl)vinylborane;
(4,5-dihexylimidazole)-di(2-methylphenyl)allylborane;
(4,5-dimethylimidazole)-di(3-isopropylphenyl)(2-methylbut-4-enyl)borane;
(4,5-dimethylimidazole)-di(4-fluorophenyl)(5,5,5-trifluoropent-3-enyl)borane;
(4,5-diethylimidazole)-di(3-chlorophenyl)(4-chloro-5-fluorohex-2-enyl)borane;
(4,5-dihexylimidazole)-di(2-chlorophenyl)vinylborane;
(4,5-dipropylimidazole)-di(2-methoxyphenyl)(2-methylbut-4-enyl)borane;
imidazole-phenyl(m-tolyl)allylborane;
imidazole-(3-methoxyphenyl)phenyl(2-methylbut-4-enyl)borane;
imidazole-(4-chlorophenyl)phenyl(5,5,5-trifluoropent-3-enyl)borane;
imidazole-(2-t-butylphenyl)phenyl(4-chloro-5-fluorohex-2-enyl)borane;
(1-ethylimidazole)-phenyl(2-trifluoromethylphenyl)-vinylborane;
(1-decylimidazole)-(2-ethylphenyl)phenylallylborane;
(1-hydroxymethylimidazole)-(2-ethoxylphenyl)phenylvinylborane;
[1-(2-ethyl-4,6-dimethylheptyl)imidazole]-(4-ethylthiophenyl)phenyl(5,5,5-trifluoropent-3-enyl)borane;
(1-cyclopropylimidazole)-[4-(2-bromo-3-fluoropropyl)phenyl]phenyl(4-chloro-5-fluorohex-2-enyl)borane;
(1-cyanomethylimidazole)-(4-isopropylphenyl)phenylvinylborane;
(1-methoxymethylimidazole)-(3-isopropylthiophenyl)phenyl(5,5,5-trifluoropent-3-enyl)borane;
(1-phenylimidazole)-(2-propylphenyl)phenyl(4-chloro-5-fluorohex-2-enyl)borane;
[1-(2-phenylethyl)imidazole]-(3-fluorophenyl)phenylvinylborane;
[1-(4-bromophenyl)imidazole]-(4-methoxylphenyl)phenylallylborane;
[1-(2,6-dimethylphenyl)imidazole]-(3-isopropylthiophenyl)phenyl(4-chloro-5-fluorohex-2-enyl)borane;
[1-(2-chloro-4-fluorophenyl)imidazole]-(2-ethylphenyl)phenylvinylborane;
[1-(4-fluoro-2-methylphenyl)imidazole]-(3-2'-chloro,3'-bromobutylphenyl)phenylallylborane;
(1-[2-(1,3-dioxolan-2-yl)butyl]imidazole)-diphenylallylborane;
[1-(2-ethoxypropyl)imidazole]-(4-ethoxyphenyl)-phenyl(2-methylbut-4-enyl)borane;
[1-(3-isopropoxypropyl)imidazole]-(3-methylthiophenyl)phenyl(5,5,5-trifluoropent-3-enyl)borane;
[1-(2-phenylethyl)imidazole]-(4-trifluoromethylphenyl)phenylvinylborane;
[5-(4-methylpentyl)imidazole]-phenyl(p-tolyl)(5,5,5-trifluoropent-3-enyl)borane;
(5-t-butylimidazole)-(4-t-butoxyphenyl)phenylvinylborane;
(5-ethylimidazole)-(3-chlorophenyl)phenylallylborane;
(5-methylimidazole)-(2-methoxylphenyl)phenyl(2-methylbut(4-enyl)borane;
imidazole-(2-ethylphenyl)(3-isopropylphenyl)(2-methylbut-4-enyl)borane;
imidazole-(4-fluorophenyl)(3-fluorophenyl)(5,5,5-trifluoropent-3-enyl)borane;
imidazole-(3-chlorophenyl)(3-fluorophenyl)(4-chloro-5-fluorohex-2-enyl)borane;
(1-octylimidazole)-(2-chlorophenyl)(2)-methylthiophenyl)vinylborane;
(1-dodecylimidazole)-(2-methoxyphenyl)(2-2',2'-dichloroethylphenyl)(2-methylbut-4-enyl)borane;
(1-ethyl-4,6-methylheptylimidazole)-(2-t-butylthiophenyl)(3-ethylphenyl)(5,5,5-trifluoropent-3-enyl)borane;
1-cyclopropylimidazole)-(2-methoxyphenyl)(4-1',1',2',2'-tetrachloroethylphenyl)(4-chloro-5-fluorohex-2-enyl)borane;
(1-cyanomethylimidazole)-(3-trifluoromethylphenyl)(4-trifluoromethylphenyl)vinylborane;

[1-(2-cyanopropyl)imidazole]-(2-methylphenyl)(4-methylphenyl)allylborane;
[1-(4-cyanobutyl)imidazole]-di(3-isopropylphenyl)(2-methylbut-4-enyl)borane;
(2-benzylimidazole)-(2-ethylphenyl)(3-trifluoromethylphenyl)vinylborane;
[2-(4-bromobenzyl)imidazole]-(2-methylphenyl)(4-proxyphenyl)allylborane;
[2-(2,4-dichlorobenzyl)imidazole]-(2-chlorophenyl)(2-fluorophenyl)ethylborane;
[2-(3-fluoro-5-ethylbenzyl)imidazole]-(2-methoxyphenyl)(2-methylthiophenyl)butylborane;
[5-(4-methylpentyl)imidazole]-(4-t-butylthiophenyl)(3-chlorophenyl)5,5,5-trifluoropent-3-enyl)borane;
(1,2-dimethylimidazole)-phenyl(3-propylphenyl)vinylborane;
[1-(4-hexylphenyl)-5-β-phenylethylimidazole]-phenyl(2fluorophenyl)(5,5,5-trifluoropent-3-enyl)borane;
(1-[2-(1,3-dioxolan-2-yl)ethyl]-5-methylimidazole)-(4-isopropylthiophenyl)phenyl(4-chloro-5-fluorohex-2-enyl)borane;
[2-(3-fluoro-5-ethylbenzyl)-5-phenylimidazole]-phenyl(3-trifluoromethylphenyl)allylborane;
(1-cyanomethyl-5-methylimidazole)-(2-chlorophenyl)(3-trifluoromethylphenyl)vinylborane;
[1-(2-cyanopropyl)-5-methylimidazole]-(2-methylphenyl)(2methoxyphenyl)allylborane;
(1-phenyl-5-phenylimidazole)-(3-methylphenyl)(4-trifluoromethylphenyl)(4-chloro-5-fluorohex-2-enyl)borane;
(2-benzyl-5-methylimidazole)-(2-methoxyphenyl)(3-trifluoromethylphenyl)vinylborane;
(4,5-dihexylimidazole)-(3-chlorophenyl)(4-isopropylphenyl)(4-chloro-5-fluorohex-2-enyl)borane; and
(4,5-dipropylimidazole)-(2-methoxyphenyl)(2-1',2'2'-trichloroethylphenyl)(2-methylbut-4-enyl)borane.

Examples 3-5 illustrate the preparation of the present compounds via the P. Kenny exchange procedure.

EXAMPLE 3

(1-Isopropenylimidazole)-Diphenylvinylborane

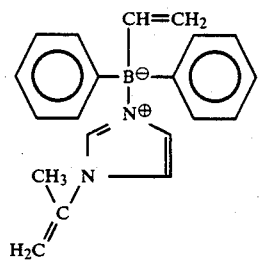

a. 150 mL's of a 1.0M vinylmagnesium bromide solution in THF is added over 30 minutes to a solution of 11.25 g (50 mmol) diphenylboronic acid ethanolamine complex in 100 mL's of THF. The addition is conducted so that the reaction mixture became warm to the touch but did not reflux. After stirring for two hours and cooling to room temperature 8.0 mL, 57 mmol of triethylamine is added and the reaction stirred overnight at room temperature. 125 mL of a saturated aqueous solution of ammonium chloride is carefully added dropwise to quench the reaction. 10 to 20 mL of water is added after the addition to solubilize the solids that had formed. The quenched reaction is stirred vigorously for two hours at room temperature whereupon the resulting liquid-liquid layers are separated and the aqueous layer extracted with 100 mL of ether. The combined organic layers are washed with 100 mL of saturated aqueous sodium chloride solution, dried over magnesium sulfate, filtered, and concentrated to give a yellow paste. The paste is triturated overnight with 60 mL of ohloroform, and the resulting crystals are isolated by suction filtration to give one crop of diphenylmethylboron-ammonia complex as a white solid, 5.65 g, 27 mmol, 54%, m.p. 169-172° C.

b. 1.51 g (7.22 mmol) of diphenylvinylboron-ammonia complex and 780 milligrams (7.22 mmol) of 1-isopropenylimidazole in 50 mL of chloroform is stirred at room temperature for one hour. The chloroform is removed by evaporation under reduced pressure and the resultant white solid triturated with 25 mL of methanol overnight. The resulting crystals are collected via suction filtration and dried in vacuo to afford 1.9 g of the title compound, m.p. 149°-150° C.

Similarly, by following the same general procedure using the appropriate starting materials, the following compounds can be prepared:
imidazole-diphenylhex-3-enylborane;
imidazole-diphenyl(3-chloroallyl)borane;
imidazole-diphenyl(3-bromobut-2-enyl)borane;
imidazole-diphenyl(3-methylbut-4-enyl)borane;
(1-octylimidazole)-diphenyl(1-isopropenyl)borane;
(1-decylimidazole)-diphenylhex-3-enylborane;
(1-dodecylimidazole)-diphenyl(3-chloroallyl)borane;
[1-(2-ethyl-4,6-dimethylheptyl)imidazole]-diphenyl(3-bromobutenyl)borane;
(1-cyclopropylimidazole)-diphenyl(3-methylbut-1-enyl)borane;
(1-cyanomethylimidazole)-diphenylisopropenylborane;
[1-(2-cyanopropyl)imidazole]-diphenylhex-3-enylborane;
[1-(4-cyanobutyl)imidazole]-diphenyl(3-chloroallyl)borane;
(1-methoxymethylimidazole)-diphenyl(3-bromobut-2-enyl)borane;
(1-phenylimidazole)-diphenyl(3-methylbut-1-enyl)borane;
[1-(2-phenylethyl)imidazole]-diphenyl(1-isopropenyl)borane;
[1-(4-bromophenyl)imidazole]-diphenylhex-3-enylborane;
[1-(4-chlorophenyl)imidazole]-diphenyl(3-chloroallyl)borane;
[1-(4-hexylphenyl)imidazole-diphenyl(3-bromo-2-enyl)borane;
[1-(2,6-dimethylphenyl)imidazole]-diphenyl(3-methylbutlenyl)borane;
[1-(2-chloro-4-fluorophenyl)imidazole]-diphenyl(1-isopropenyl)borane;
[1-(4-fluoro-2-methylphenyl)imidazole]-diphenylhex-3-enylborane;
[1-(3-chloroallyl)imidazole]-diphenyl(chloroallyl)borane;
[1-(2-fluoropent-2-enyl)imidazole]-diphenyl(3-bromobut-2enyl)borane;
(1-[2-(1,3-dioxolan-2-yl)ethyl]imidazole)-diphenyl(3-methylbutlenyl)borane;
(1-[2-(1,3-dioxolan-2-yl)butyl]imidazole)-diphenylisopropenylborane;
(1-[2-(1,3-dioxolan-2-yl)butyl]imidazole)-diphenylhex-3enylborane;

[1-(2-ethoxypropyl)imidazole]-diphenyl(3-chloroallyl)-borane;
[1-(3-isopropoxypropyl)imidazole]-diphenyl(3-bromobut-2enyl)borane;
[1-(2-phenylethyl)imidazole]-(3-methylbut-1-enyl)borane;
(2-benzylimidazole)-diphenylisopropenylborane;
[2-(4-bromobenzyl)imidazole]-diphenyl(hex-3-enyl)borane;
(2-ethylbenzyl)imidazole-diphenyl(3-chloroallyl)borane;
[2-(2-bromobenzyl)imidazole]-diphenyl(3-bromobut-2-enyl)borane;
[2-(2,6-dimethylbenzyl)imidazole]-diphenyl(3-methylbut-1enyl)borane;
[2-(2,4-dichlorobenzyl)imidazole]-diphenylisopropenylborane;
[2-(3-fluoro-5-ethylbenzyl)imidazole]-diphenylhex-3-enylborane;
[2-(2-chloro-3-iodobenzyl)imidazole]-diphenyl(3-chloroallyl)borane;
[5-(4-methylpentyl)imidazole]-diphenyl(3-bromobut-2-enyl)borane;
(5-isopropylimidazole)-diphenyl(3-methylbut-1-enyl)-borane;
(5-t-butylimidazole)-diphenylisopropenylborane;
(5-ethylimidazole)-diphenylhex-3-enylborane;
(5-methylimidazole)-diphenyl(3-chloroallyl)borane;
(5-isopropylimidazole)-diphenyl(3-bromobut-2-enyl)-borane;
(5-hexylimidazole)-diphenyl(3-methylbut-1-enyl)-borane;
(5-ethylimidazole)-diphenylisopropenylborane;
(5-isopropylimidazole)-diphenylhex-3-enylborane;
(5-t-butylimidazole)-diphenyl(3-chloroallyl)borane;
imidazole-di(2-methylphenyl)hex-3-enylborane;
imidazole-di(3-isopropylphenyl)(3-chloroallyl)borane;
imidazole-di(4-fluorophenyl)3-bromobut-2-enyl)borane;
(1-octylimidazole)-di(2-chlorophenyl)isopropenylborane;
(1-dodecylimidazole)-di(2-methoxyphenyl)(3-chloroallyl)borane;
(1-2'-ethyl-4',6'-dimethylheptylimidazole)-di(2-t-butylthiophenyl)(3-bromobut-2-enyl)borane;
(1-cyanomethylimidazole)-di(3-trifluoromethylphenyl)(1- L isopropenyl)borane;
[1-(2-cyanopropyl)imidazole]-di(2-methylphenyl)hex-3-enylborane;
[1-(4-cyanobutyl)imidazole]-di(3-isopropylphenyl)(3-chloroallyl)borane;
(1-methoxymethylimidazole)-di(4-fluorophenyl)(3-bromobut-2-enyl)borane;
[1-(2-phenylethylimidazole)-di(2-chlorophenyl)isopropenylborane;
[1-(2-chlorophenyl)imidazole]-di(2-methoxyphenyl)(3-chloroallyl)borane;
[1-(4-hexylphenyl)imidazole]-di(4-t-butylthiophenyl)(3
[1-(2-chloro-4-fluorophenyl)imidazole]-di(3 phenyl)isopropenylborane;
[1-(1-fluoro-2-methylphenyl)imidazole]-di(2-methylphenyl)hex-3-enylborane;
[1-(3-chloroallyl)imidazole]-di(3-isopropylphenyl)(3-chloroallyl)borane;
[1-(2-fluoropent-2-enyl)imidazole]-di(4-fluorophenyl)(3-bromobut-2-enyl)borane;
(1-[2-(1,3-dioxolan-2-yl)butyl]imidazole)-di(2-chlorophenyl)(1-isopropenyl)borane;
[1-(2-ethoxypropyl)imidazole]-di(2-methoxyphenyl)(3-chloroallyl)borane;
[1-(3-isopropylpropoxy)imidazole]-di(4-t-butylthiophenyl)(3-bromobut-2-enyl)borane;
(2-benzyl)imidazole]-di(3-trifluoromethylphenyl)isopropenylborane;
[2-(4-bromobenzyl)imidazole]-di(2-methylphenyl)hex-3-enylborane;
[2-(3-ethylbenzyl)imidazole]-di(3-isopropylphenyl)(3-chloroallyl)borane;
[2-(2-bromobenzyl)imidazole]-di(4-fluorophenyl)(3-bromobut-2-enyl)borane;
[2-(2,4-dichlorobenzyl)imidazole]-di(2-chlorophenyl)(1-isopropenyl)borane; [2,(3-fluoro-5-ethylbenzyl)imidazole]-di(2-fluorophenyl)hex3-enylborane;
[2-(2-chloro-3-iodobenzyl)imidazole]-di(2-methoxyphenyl)(3chloroallyl)borane;
[5-(4-methylpentyl)imidazole]-di(4-t-butylthiophenyl)(3-bromobut-2-enyl)borane;
(5-t-butylimidazole)-di(3-trifluoromethylphenyl)isopropenylborane;
(5-ethylimidazole)-di(2-methylphenyl)hex-3-enylborane;
(5-methylimidazole)-di(3-isopropylphenyl)(3-chloroallyl)borane;
(5-isopropylimidazole)-di(4-fluorophenyl)(3-bromobut-2enyl)borane;
4 (5-ethylimidazole)-di(2-chlorophenyl)isopropenylborane;
(5-t-butylimidazole)-di(2-methoxyphenyl)(3-chloroallyl)borane;
(1-ethyl-2-isopropylimidazole)-diphenylhex-3-enylborane;
(1-isopropyl-2-methylimidazole)-diphenyl(3-chloroallyl)borane;
(1-butyl-2-phenylimidazole)-diphenyl(3-bromobut-2-enyl)borane;
(1,2-diphenylimidazole)-diphenyl(3-methylbut-4-enyl)-borane;
(1-octyl-2-phenylimidazole)-diphenyl(1-isopropenyl)-borane;
(1-decyl-2-phenylimidazole)-diphenylhex-3-enylborane;
(1-dodecyl-2-phenylimidazole)-diphenyl(3-chloroallyl)-borane;
[1-(2-ethyl-4,6-dimethylheptyl)-2-phenylimidazole]-dipheny (3-bromobutenyl)borane;
(1-cyclopropyl-2-phenylimidazole)-diphenyl(3-methylbut-1enyl)borane;
(1-cyanomethyl-2-phenylimidazole)-diphenylisopropenylborane;
[1-(2-cyanopropyl)-2-phenylimidazole]-diphenylhex-3-enylborane;
[1-(4-cyanobutyl)-2-phenylimidazole]-diphenyl(3-chloroallyl)borane;
(1-methoxymethyl-2-phenylimidazole)-diphenyl(3-bromobut-2enyl)borane;
(1-phenyl-2-phenylimidazole)-diphenyl(3-methylbut-1-enyl)borane;
[2-p-chlorobenzyl-1-(2-phenylethyl)imidazole]-diphenyl(1-isopropenyl)borane;
[1-(4-bromophenyl)-2-(2,6-dimethylbenzylimidazole]-diphenylhex-3-enylborane;
[1-(2-chlorophenyl)-5-methylimidazole]-diphenyl(3-chloroallyl)borane;
[1-(4-hexylphenyl)-5-methylimidazole]-diphenyl(3-bromo-2-enyl)borane;

[1-(2,6-dimethylphenyl)-5-methylimidazole]-diphenyl(3-methylbut-1-enyl)borane;
[1-(2-chloro-4-fluorophenyl)-5-methylimidazole]-diphenyl(1-isopropenyl)borane;
[1-(4-fluoro-2-methylphenyl)-5-methylimidazole]-diphenylhex-3-enylborane;
[1-(3-chloroallyl)-5-methylimidazole]-diphenyl(3-chloroallyl)borane;
(1-ethyl-5-isopropylimidazole)-diphenyl(3-chloroallyl)borane;
(5-ethyl-1-vinylimidazole)-diphenyl(3-chloroallyl)borane;
[1-(2-fluoropent-2-enyl)-5-phenylimidazole]-diphenyl(3-bromobut-2-enyl)borane;
(1-[2-(1,3-dioxolan-2-yl)ethyl]-5-phenylimidazole]-diphenyl(3-methylbut-1-enyl)borane;
(1-[2-(1,3-dioxolan-2-yl)butyl]-5-phenylimidazole]-diphenylisopropenylborane;
(1-[2-(1,3-dioxolan-2-yl)butyl]-5-phenylimidazole]-diphenylhex-3-enylborane;
[1-(2-ethoxypropyl)-5-phenylimidazole]-diphenyl(3-chloroallyl)borane;
[1-(3-isopropoxypropyl)-5-phenylimidazole]-diphenyl(3-bromobut-2-enyl)borane;
[1-(2-phenylethyl)-5-phenylimidazole]-3-methylbut-1-enyl)borane;
(2-benzyl-5-methylimidazole)-diphenylisopropenylborane;
[2-(4-bromobenzyl)-5-methylimidazole]-diphenylhex-3-enylborane;
[(2-ethylbenzyl)-5-methylimidazole]-diphenyl(3-chloroallyl)borane;
[2-(2-bromobenzyl)-5-methylimidazole]-diphenyl(3-bromobut-2enyl)borane;
[2-(2,6-dimethylbenzyl)-5-methylimidazole]-diphenyl(3-methylbut-1-enyl)borane;
[2-(2,4-dichlorobenzyl)-5-methylimidazole]-diphenylisopropenylborane;
[2-(3-fluoro-5-ethylbenzyl)-5-methylimidazole]-diphenylhex-3-enylborane;
[2-(2-chloro-3-iodobenzyl)-5-methylimidazole]-diphenyl(3chloroallyl)borane;
[4,5-di(4-methylpentyl)-imidazole]-diphenyl(3-bromobut-2-enyl)borane;
(4,5-dipropylimidazole)-diphenyl(3-methylbut-1-enyl)borane;
(4,5-diisopropylimidazole)-diphenylisopropenylborane;
(4,5-dipentylimidazole)-diphenylhex-3-enylborane;
(5-methylimidazole)-diphenyl(3-chloroallyl)borane;
(4,5-dimethylimidazole)-diphenyl(3-bromobut-2-enyl)borane;
(4,5-dihexylimidazole)-diphenyl(3-methylbut-1-enyl)borane;
[4,5-diethylimidazole)-diphenylisopropenylborane;
(4,5-diisopropylimidazole)-diphenylhex-3-enylborane;
(5-t-butylimidazole-diphenyl(3-chloroallyl)borane;
dazole)-di(2-chlorophenyl)isopropenylborane;
(1-dodecyl-5-methylimidazole)-di(2-methoxyphenyl)(3-chloroallyl)borane;
(1-ethyl-4,6-dimethylheptyl-5-methylimidazole)-di(2-t-butylthiophenyl)(3-bromobut-2-enyl)borane;
(1-cyanomethyl-5-propylimidazole)-di(3-trifluoromethylphenyl)-(1-isopropenyl)borane;
[1-(2-cyanopropyl)-5-propylimidazole]-di(2-methylphenyl)hex-3-enylborane;
[1-(4-cyanobutyl)-5-propylimidazole]-di(3-isopropylphenyl)-(3-chloroallyl)borane;
(1-methoxymethyl-5-propylimidazole)-di(4-fluorophenyl)(3-bromobut-2-enyl)borane;
[1-(2-phenylethyl)-5-propylimidazole]-di(2-chlorophenyl)isopropenylborane;
[1-(2-chlorophenyl)-5β-phenylethylimidazole]-di(2-methoxyphenyl)-(3-chloroallyl)borane;
[1-(4-hexylphenyl)-5-pentylimidazole]-di(4-t-butylthiophenyl)-(3-bromobut-2-enyl)borane;
[1-(2-chloro-4-fluorophenyl)-5-hexylimidazole]-di(3-trifluoromethylphenyl)isopropenylborane;
[1-(1-fluoro-2-methylphenyl)-5-hexylimidazole]-di(2-methylphenyl)hex-3-enylborane;
[1-(3-chloroallyl)-5-hexylimidazole]-di(3-isopropylphenyl)(3-chloroallyl)borane;
[1-(2-fluoropent-2-enyl)-5-hexylimidazole]-di(4-fluorophenyl)(3-bromobut-2-enyl)borane;
(1-[2-(1,3-dioxolan-2-yl)butyl]-5-hexylimidazole]-di(2-chlorophenyl)(1-isopropenyl)borane;
[1-(2-ethoxypropyl)-5-(3-phenylpentyl)imidazole]-di(2-methoxyphenyl)(3-chloroallyl)borane;
[1-(3-isopropoxypropyl)-5-(2-pentyl)imidazole]-di(4-t-butylthiophenyl)(3-bromobut-2-enyl)borane;
(2-benzyl-5-methylimidazole)-di(3-trifluoromethylphenyl)isopropenylborane;
[1-(4-bromobenzyl)-5-methylimidazole]-di(2-methylphenyl)hex-3-enylborane;
[2-(3-ethylbenzyl)-5-methylimidazole]-di(3-isopropylphenyl)-(3-chloroallyl)borane;
2-(2-bromobenzyl)-5-methylimidazole]-di(4-fluorophenyl)(3-bromobut-2-enyl)borane;
[2-(2,4-dichlorobenzyl)-5-methylimidazole]-di(2-chlorophenyl)-(1-isopropenyl)borane;
[2-(3-fluoro-5-ethylbenzyl)-5-methylimidazole]-di(2-fluorophenyl)hex-3-enylborane;
[2-(2-chloro-3-iodobenzyl)-5-methylimidazole]-di(2-methoxyphenyl)-(3-chloroallyl)borane;
(4,5-dimethylimidazole)-di(3-trifluoromethylphenyl)isopropenylborane;
(4,5-diisopropylimidazole)-di(2-methylphenyl)hex-3-enylborane;
imidazole-phenyl(p-tolyl)hex-3-enylborane;
imidazole-(2-ethylphenyl)phenyl(3-chloroallyl)borane;
(1-methoxymethylimidazole)-(4-butyoxyphenyl)-phenyl(3-bromobut-2-enyl)borane;
[1-(2-fluoropent-2-enyl)imidazole]-(3-fluorophenyl)-phenyl(3-bromobut-2-enyl)borane;
(1-[2-(1,3-dioxolan-2-yl)butyl]imidazole)-(2-methylthiophenyl)phenylisopropenylborane;
(1-[2-(1,3-dioxolan-2-yl)butyl]imidazole)-diphenylhex-3enylborane;
[1-(2-ethoxypropyl)imidazole]-(3-trifluoromethylphenyl)phenyl(3-chloroallyl)borane;
(2-benzylimidazole)-(4-methylphenyl)phenylisopropenylborane; (2-ethylbenzyl)imidazole-(3-methoxyphenyl)phenyl(3-chloroallyl)borane;
[2-(3-fluoro-5-ethylbenzyl)imidazole]-(2-ethylthiophenyl)phenylhex-3-enylborane;
[5-(4-methylpentyl)imidazole]-(4-ethylphenyl)-phenyl(3-bromobut-2-enyl)borane;
(5-isopropylimidazole)-phenyl(-tolyl)(3-methylbut-1-enyl)borane;
imidazole-(2-methylphenyl)(3-chlorophenyl)hex-3-enylborane;
imidazole-(3-isopropylphenyl)(2-t-butoxyphenyl)(3-chloroallyl)borane;
(1-cyanomethylimidazole)-(2-fluorophenyl)(3-trifluoromethylphenyl)(1-isopropenyl)borane;

(1-methoxymethylimidazole)-(4-fluorophenyl)(4-propylthiophenyl)(3-bromobut-2-enyl)borane;
[1-(2-phenylethylimidazole)-(2-chlorophenyl)(3-trifluoromethylphenyl)isopropenylborane;
[(2-benzyl)imidazole]-(4-butylphenyl)(3-trifluoromethylphenyl)isopropenylborane;
[2,(3-fluoro-5-ethylbenzyl)imidazole]-(2-fluorophenyl)(3-methoxyphenyl)hex-3-enylborane;
[5-(4-methylpentyl)imidazole]-(4-butylphenyl)(4-t-butylthiophenyl)(3-bromobut-2-enyl)borane;
(1-ethyl-2-isopropylimidazole)-phenyl(m-tolyl)hex-3-enylborane;
(1-isopropyl-2-methylimidazole)-(4-fluorophenyl)-phenyl(3-chloroallyl)borane;
[1-(2-ethyl-4,6-dimethylheptyl)-2-phenylimidazole](3-isopropylthiophenyl)phenyl(3-bromobutenyl)borane;
(1-cyclopropyl-2-phenylimidazole)-(4-2',2'-dibromoethylphenyl)phenyl(3-methylbut-1-enyl)borane;
[1-(2-chlorophenyl)-5-methylimidazole]-phenyl(p-tolyl)(3-chloroallyl)borane;
[1-(3-chloroallyl)-5-methylimidazole]-(2-trifluoromethylphenyl)phenyl(3-chloroallyl)borane;
(2-benzyl-5-methylimidazole)-(2-ethylphenyl)-phenylisopropenylborane;
[(2-ethylbenzyl)-5-methylimidazole]-(4-butoxyphenyl)-phenyl(3-chloroallyl)borane;
(4,5-propylimidazole)-(4-fluorophenyl)phenyl(3-methylbut-1-enyl)borane;
(1-dodecyl-5-methylimidazole)-(2-methoxyphenyl)(4-t-butylthiophenyl)(3-chloroallyl)borane;
(2-benzyl-5-methylimidazole)-(4-propylphenyl)(3-trifluoromethylphenyl)isopropenylborane;
[2-(4-bromobenzyl)-5-methylimidazole]-(3-fluorophenyl)(2-methylphenyl)hex-3-enylborane;
(4,5-methylimidazole)-(4-isopropylthiophenyl)(3-trifluoromethylphenyl)isopropenylborane; and
(5-ethyl-4-isopropylimidazole)-(2-methylphenyl)(2-methoxyphenyl)hex-3-enylborane.

EXAMPLE 4

Imidazole-Diphenylmethylborane

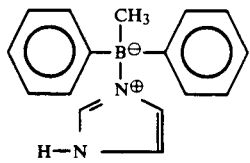

In this example, 1.23 g (6.2 mmol) of diphenylmethylboronammonia complex is added to 50 mL of chloroform at room temperature followed by the addition of 0.42 g (6.2 mmol) of imidazole. The resulting mixture was heated at reflux for four hours. After cooling in an ice bath, a white solid precipitated which was collected by filtration and washed with cold chloroform. The white solid is dried in vacuo, 1.15 g (83% yield), m.p. 154°–156° C.

Similarly, by following the same general procedure using the appropriate starting materials, the following compounds can be prepared:
(1-hydroxymethylimidazole)-diphenylethylborane;
[1-(5-hydroxypentylimidazole)]-diphenylmethylborane;
[1-(4-hydroxyhexylimidazole)]-diphenylisopropylborane;
imidazole-diphenylethylborane;
imidazole-diphenylbutylborane;
imidazole-diphenylisopropylborane;
imidazole-diphenylcyclohexylborane;
(1-octylimidazole)-diphenylmethylborane;
(1-decylimidazole)-diphenylethylborane;
(1-dodecylimidazole)-diphenylbutylborane;
[1-(2-ethyl-4,6-dimethyl)heptylimidazole]-diphenylisopropyl borane;
(1-cyclopropylimidazole)-diphenylcyclohexylborane;
(1-cyanomethylimidazole)-diphenylmethylborane;
[1-(2-cyanopropyl)imidazole]-diphenylethylborane;
[1-(4-cyanobutyl)imidazole]-diphenylbutylborane;
(1-methoxymethylimidazole-diphenylisopropylborane;
(1-phenylimidazole)-diphenylcyclohexylborane;
[1-(2-phenylethyl)imidazole]-diphenylmethylborane;
[1-(4-bromophenyl)imidazole]-diphenylethylborane;
[1-(2-chlorophenyl)imidazole]-diphenylisopropylborane;
[1-(4-hexylphenyl)imidazole-diphenylcyclohexylborane;
[1-(2,6-dimethylphenyl)imidazole-diphenylmethylborane;
[1-(2-chloro-4-fluorophenyl)imidazole]-diphenylethylborane;
[1-(4-fluoro-2-methylphenyl)imidazole-diphenylbutylborane;
[1-(3-chloroallyl)imidazole-diphenylisopropylborane;
[1-(2-fluoropent-2-enyl)imidazole]-diphenylcyclohexylborane;
(1-[2-(1,3-dioxolan-2-yl)ethyl]imidazole)-diphenylmethylborane;
(1-[2-(1,3-dioxolan-2-yl)butyl]imidazole-diphenylethylborane;
(1-[2-(1,3-dioxolan-2-yl)butyl]imidazole)-diphenylbutylborane;
1-(2-ethoxypropyl)imidazole]-diphenylisopropylborane;
(2-phenylimidazole)-diphenyl(fluoromethyl)borane;
(2-benzylimidazole)-diphenyl(1,2-dichloroethyl)borane;
2-(4-bromobenzyl)imidazole]-diphenylbutylborane;
2-(3-ethylbenzyl)imidazole]-diphenylisopropylborane;
[2-(2-bromobenzyl)imidazole]-diphenylcyclohexylborane;
[2-(2,6-dimethylbenzyl)imidazole]-diphenyl(trifluoro)borane;
[2-(2,4-dichlorobenzyl)imidazole]-diphenylethylborane;
[2-(3-fluoro-5-ethylbenzyl)imidazole]-diphenyl(3-chloro-4fluorobutyl)borane;
[2-(2-chloro-3-iodobenzyl)imidazole]-diphenylcyclohexylborane;
[5-(4-methylpentyl)imidazole]-diphenylmethylborane;
(5-isopropylimidazole)-diphenylethylborane;
(5-t-butylimidazole)-diphenylbutylborane;
(5-ethylimidazole)-diphenylisopropylborane;
(5-methylimidazole)-diphenylcyclohexylborane;
(5-isopropylimidazole)-diphenylmethylborane;
(5-hexylimidazole)-diphenylethylborane;
(5-ethylimidazole)-diphenylbutylborane;
(5-isopropylimidazole)-diphenylisopropylborane;
(5-t-butylimidazole)-diphenylcyclohexylborane;
imidazole-di(2-methylphenyl)ethylborane;
imidazole-di(3-isopropylphenyl)butylborane;
imidazole-di(4-fluoropentyl)isopropylborane;
(1-octylimidazole)-di(2-chlorophenyl)methylborane;
(1-dodecylimidazole)-di(2-methoxyphenyl)butylborane;
[1-(2-ethyl-4,6-dimethylheptyl)imidazole]-di(4-t-butylthiophenyl)isopropylborane;

(1-cyanomethylimidazole)-di(3-trifluoromethylphenyl)-
methylborane;
[1-(2-cyanopropyl)imidazole]-di(2-methylphenyl)ethyl-
borane;
[1-(4-cyanobutyl)imidazole]-di(3-isopropylphenyl)-
butylborane;
(1-methoxymethylimidazole)-di(4-fluorophenyl)iso-
propylborane;
[1-(2-phenylethyl)imidazole]-di(2-chlorophenyl)me-
thylborane;
[1-(4-bromophenyl)imidazole]-di(3-fluorophenyl)ethyl-
borane;
[1-(2-chlorophenyl)imidazole]-di(2-methoxyphenyl)iso-
propylborane;
[1-(4-hexylphenyl)imidazole]-di(4-t-butylthiophenyl)-
cyclohexylborane;
[1-(2-chloro-4-fluorophenyl)imidazole]-di(3-tri-
fluoromethylphenyl)ethylborane;
[1-4-fluoro-2-methylphenyl)imidazole]-di(2-methyl-
phenyl)butylborane;
[1-(3-chloroallyl)imidazole]-di(isopropylphenyl)iso-
propylborane;
[1-(2-fluoropent-2-enyl)imidazole]-di(2-fluorophenyl)-
cyclohexylborane;
(1-[2-(1,3-dioxolan-2-yl)butyl]imidazole)-di(2-chloro-
phenyl)ethylborane;
[1-(2-ethoxypropyl)imidazole]-di(2-methoxyphenyl)iso-
propylborane;
[1-(3-isopropylpropoxy)imidazole]-di(4-butylthio-
phenyl)cyclohexylborane;
(2-benzylimidazole)-di(3-trifluoromethylphenyl)ethyl-
borane;
[2-(4-bromobenzyl)imidazole]-di(2-methylphenyl)-
butylborane;
[2-(3-ethylbenzyl)imidazole]-di(3-isopropylphenyl)iso-
propylborane;
2-(2-bromobenzyl)imidazole]-di(4-fluorophenyl)cy-
clohexylborane;
[2-(2,4-dichlorobenzyl)imidazole]-di(2-chlorophenyl)e-
thylborane;
[2-(2-chloro-3-iodobenzyl)imidazole-di(2-methoxy-
phenylcyclohexylborane;
[5-(4-methylpentyl)imidazole]-di(4-t-butylthiophenyl)-
methylborane;
(5-t-butylimidazole)-di(2-methylphenyl)butylborane;
(5-ethylimidazole)-di(3-trifluoromethylphenyl)ethylbo-
rane;
(5-methylimidazole)-di(3-isopropylphenyl)cyclohexyl-
borane;
(5-isopropylimidazole-di(4-fluorophenyl)methylborane;
(5-ethylimidazole)-di(2-chlorophenyl)isopropylborane;
(5-t-butylimidazole)-di(2-methoxyphenyl)cyclohexyl-
borane;
(1-hydroxymethylimidazole-(4-isopropylphenyl)-
phenylethylborane;
(5 imidazole-(2-methoxyphenyl)phenylisopropylbo-
rane;
(2-phenylimidazole)-(3-fluorophenyl)phenylmethylbo-
rane;
(5-isopropylimidazole)-(4-ethylthiophenyl)phenyl(2,2-
fluoroethyl)borane;
imidazole-(3-isopropylphenyl)(2-trifluoromethyl-
phenyl)butylborane;
(1-cyanomethylimidazole)-(4-propylphenyl)(3-tri-
fluoromethylphenyl)methylborane; and
(5-t-butylimidazole)-(2-methylthiophenyl)(2-methoxy-
phenyl)cyclohexylborane.

EXAMPLE 5

(1-Isopropenylimidazole)-Diphenylmethylborane

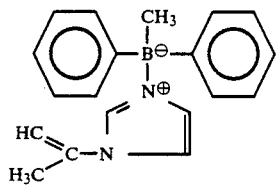

In this example, 1.39 g (7.03 mmol) of diphenylme-
thylboronammonia complex, 760 milligrams (7.03
mmol) of 1-isopropenylimidazole, and 50 mL of chloro-
form are stirred at room temperature for one hour. The
chloroform is removed by evaporation under reduced
pressure and the resultant white solid triturated over-
night with 25 mL of methanol. The crystals are col-
lected by suction filtration and dried in vacuo to pro-
vide 1.9 g of the title compound,

EXAMPLE 6

Similarly, by applying the same general procedures
using the appropriate starting materials, the compounds
identified in Table A below are prepared:

TABLE A

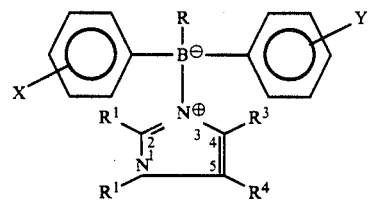

| No. | R | $R^1$ | $R^2$ | $R^3$ | $R^4$ | X | Y | Melting Point °C. |
|---|---|---|---|---|---|---|---|---|
| 1 | $CH_3$ | H | H | H | H | H | H | 154–156 |
| 2 | $CH_3$ | H | H | H | H | 4-$CH_3$ | 4-$CH_3$ | 141–144 |
| 3 | $CH_3$ | H | H | H | H | 4-Cl | 4-Cl | oil |
| 4 | $CH_3$ | H | $CH_3$ | H | H | H | H | 163–166 |
| 5 | $CH_3$ | $CH_3$ | H | H | H | H | H | 124–126 |
| 6 | $CH_3$ | H | H | H | $CH_3$ | H | H | 163–165 |
| 7 | $CH_3$ | $CH_3$ | H | H | H | 4-$CH_3$ | 4-$CH_3$ | 135–136 |
| 8 | $CH_3$ | H | $CH_3$ | H | H | 4-Cl | 4-Cl | oil |
| 9 | $CH_3$ | $CH_3$ | H | H | H | 4-Cl | 4-Cl | oil |
| 10 | $CH_3$ | H | $CH_3$ | H | H | 4-F | 4-F | oil |
| 11 | $CH_3$ | $CH_3$ | H | H | H | 4-F | 4-F | 111–113 |

TABLE A-continued

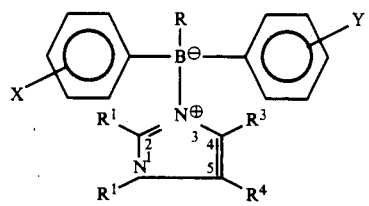

| No. | R | R¹ | R² | R³ | R⁴ | X | Y | Melting Point °C. |
|---|---|---|---|---|---|---|---|---|
| 12 | $CH_3$ | H | H | H | $CH_3$ | 4-F | 4-F | 174–175 |
| 13 | $CH_3$ | $CH_3$ | H | H | H | 4-$CF_3$ | 4-$CF_3$ | 100–102 |
| 14 | $CH_3$ | H | $CH_3$ | H | H | 4-$OCH_3$ | 4-$OCH_3$ | oil |
| 15 | $CH_3$ | $CH_3$ | H | H | H | 4-$OCH_3$ | 4-$OCH_3$ | oil |
| 16 | $CH_3$ | $CH_3$ | H | H | H | 4-$SCH_3$ | 4-$SCH_3$ | 108–112 |
| 17 | $CH_3$ | H | $C_2H_5$ | H | H | H | H | 102–104 |
| 18 | $CH_3$ | $C_2H_5$ | H | H | H | H | H | oil |
| 19 | $CH_3$ | H | $C_2H_5$ | H | H | 4-$OCH_3$ | 4-$OCH_3$ | oil |
| 20 | $CH_3$ | $CH_2CH_2CH_3$ | H | H | H | H | H | oil |
| 21 | $CH_3$ | $CH_2CH_2CH_3$ | H | H | H | 4-Cl | 4-Cl | oil |
| 22 | $CH_3$ | $CH_2CH_2CH_3$ | H | H | H | 4-$CF_3$ | 4-$CF_3$ | oil |
| 23 | $CH_3$ | H | H | H | $-CH_2CH_2CH_3$ | H | H | oil |
| 24 | $CH_3$ | $CH(CH_3)_2$ | H | H | H | H | H | 180–182 |
| 25 | $CH_3$ | $(CH_2)_3CH_3$ | H | H | H | H | H | oil |
| 26 | $CH_3$ | $CH_2CH(CH_3)_2$ | H | H | H | H | H | oil |
| 27 | $CH_3$ | H | H | H | $CH(CH_3)_2$ | H | H | 165–166 |
| 28 | $CH_3$ | H | H | H | $C(CH_3)_3$ | H | H | 205–206 |
| 29 | $CH_3$ | $(CH_2)_4CH_3$ | H | H | H | H | H | 94–95 |
| 30 | $CH_3$ | $(CH_2)_9CH_3$ | H | H | H | H | H | oil |
| 31 | $CH_3$ | $(CH_2)_2CH_3$ | $CH_3$ | H | H | H | H | solid 58–62 (decomposes) |
| 32 | $CH_3$ | $CH(CH_3)_2$ | $CH_3$ | H | H | H | H | 130–132 |
| 33 | $CH_3$ | $(CH_2)_3CH_3$ | $CH_3$ | H | H | H | H | 98–99 |
| 34 | $CH_3$ | $(CH_2)_2CH_3$ | $C_2H_5$ | H | H | H | H | 119–120 |
| 35 | $CH_3$ | $CH(CH_3)_2$ | $C_2H_5$ | H | H | H | H | 99–100 |
| 36 | $CH_3$ | $CH_3$ | $(CH_2)_3CH_3$ | H | H | H | H | oil |
| 37 | $CH_3$ | Cyclopentyl | H | H | H | H | H | 182–183 |
| 38 | $CH_3$ | $CH=CH_2$ | H | H | H | H | H | 167–170 |
| 39 | $CH_3$ | $CH_2CH=CH_2$ | H | H | H | H | H | 115–116 |
| 40 | $CH_3$ | $CH=CH_2$ | $(CH_2)_2CH_3$ | H | H | H | H | oil |
| 41 | $CH_3$ | $CH=CH_2$ | $CH_3$ | H | H | H | H | oil |
| 42 | $CH_3$ | $(CH_2)_2CH_2Cl$ | H | H | H | H | H | 110–113 |
| 43 | $CH_3$ | $-CH_2CF_3$ | H | H | H | H | H | 182–184 |
| 44 | $CH_3$ | $CH_2CH=CHCl$ | H | H | H | H | H | 113–115 - 90% trans Cl isomer |
| 45 | $CH_3$ | $CH_2C(Br)=CH_2$ | H | H | H | H | H | 145–146 |
| 46 | $CH_3$ | $CH_2CH=CCl_2$ | H | H | H | H | H | oil |
| 47 | $CH_3$ | $CH_2CN$ | H | H | H | H | H | 184–186 |
| 48 | $CH_3$ | $CH_2OCH_3$ | H | H | H | H | H | oil |
| 49 | $CH_3$ | H | H | H | φ* | H | H | 120–124 |
| 50 | $CH_3$ | $CH_2φ$ | H | H | H | H | H | 98–104 |
| 51 | $CH_3$ | $CH_2$-4-Brφ | H | H | H | H | H | 125–129 |
| 52 | Cyclopropyl | H | $CH_3$ | H | H | H | H | oil |
| 53 | Cyclopropyl | $CH_3$ | H | H | H | H | H | 140–142 |
| 54 | Cyclopropyl | H | H | H | $CH_3$ | H | H | oil |
| 55 | Cyclopropyl | $C_2H_5$ | H | H | H | H | H | 160–162 |
| 56 | Cyclopropyl | $(CH_2)_2CH_3$ | H | H | H | H | H | oil |
| 57 | Cyclopropyl | $CH(CH_3)_2$ | H | H | H | H | H | 166–167 |
| 58 | Cyclopropyl | $CH_2CH(CH_3)_2$ | H | H | H | H | H | 130–132 |
| 59 | Cyclopropyl | $CH=CH_2$ | H | H | H | H | H | oil |
| 60 | Cyclopropyl | $CH_2CH=CH_2$ | H | H | H | H | H | oil |
| 61 | Cyclopropyl | ** | H | H | H | H | H | 120–121 |
| 62 | Cyclopentyl | $CH_3$ | H | H | H | H | H | 120–124 |
| 63 | Cyclopentyl | $(CH_2)_2CH_3$ | H | H | H | H | H | 112–115 |
| 64 | Cyclopentyl | $CH(CH_3)_2$ | H | H | H | H | H | 112–114 |
| 65 | Cyclopentyl | Cyclopentyl | H | H | H | H | H | 103–104 |
| 66 | Cyclopentyl | $CH=CH_2$ | H | H | H | H | H | oil |
| 67 | Cyclopentyl | $CH_2φ$ | H | H | H | H | H | 122–124 |
| 68 | Cyclopentyl | ** | H | H | H | H | H | 133–135 |
| 69 | Cyclohexyl | $CH_3$ | H | H | H | H | H | 141–142 |
| 70 | Cyclohexyl | $(CH_2)_2CH_3$ | H | H | H | H | H | 134–136 |
| 71 | Cyclohexyl | $CH(CH_3)_2$ | H | H | H | H | H | 125–128 |
| 72 | Cyclohexyl | ** | H | H | H | H | H | 145–149 |
| 73 | $CH=CH_2$ | H | H | H | H | H | H | 128–131 |
| 74 | $CH=CH_2$ | H | H | H | H | 4-Cl | 4-Cl | oil |
| 75 | $CH=CH_2$ | H | H | H | H | 4-$CF_3$ | 4-$CF_3$ | oil |
| 76 | $CH=CH_2$ | H | $CH_3$ | H | H | H | H | oil |
| 77 | $CH=CH_2$ | $CH_3$ | H | H | H | H | H | 132–133 |
| 78 | $CH=CH_2$ | H | H | H | $CH_3$ | H | H | oil |
| 79 | $CH=CH_2$ | H | $CH_3$ | H | H | H | H | oil |

TABLE A-continued

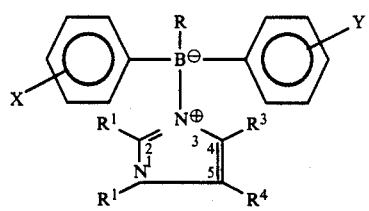

| No. | R | R¹ | R² | R³ | R⁴ | X | Y | Melting Point °C. |
|---|---|---|---|---|---|---|---|---|
| 80 | CH=CH₂ | CH₃ | H | H | H | 4-CH₃ | 4-CH₃ | oil |
| 81 | CH=CH₂ | H | CH₃ | H | H | 4-CH₃ | 4-CH₃ | oil |
| 82 | CH=CH₂ | CH₃ | H | H | H | 4-F | 4-F | oil |
| 83 | CH₂=CH₂ | CH₃ | H | H | H | 4-F | 4-F | 80–83 |
| 84 | CH₂=CH₂ | H | CH₃ | H | H | 4-Cl | 4-Cl | oil |
| 85 | CH=CH₂ | CH₃ | H | H | H | 4-Cl | 4-Cl | oil |
| 86 | CH=CH₂ | CH₃ | H | H | H | 4-SCH₃ | 4-SCH₃ | oil |
| 87 | CH=CH₂ | H | C₂H₅ | H | H | H | H | oil |
| 88 | CH=CH₂ | C₂H₅ | H | H | H | H | H | oil |
| 89 | CH=CH₂ | (CH₂)CH₃ | H | H | H | H | H | oil |
| 90 | CH=CH₂ | H | H | H | (CH₂)₂CH₃ | H | H | oil |
| 91 | CH=CH₂ | CH(CH₃)₂ | H | H | H | H | H | 150–151 |
| 92 | CH=CH₂ | (CH₂)₃CH₃ | H | H | H | H | H | oil |
| 93 | CH=CH₂ | H | CH₂CH(CH₃)₂ | H | H | H | H | oil |
| 94 | CH=CH₂ | H | C(CH₃)₃ | H | H | H | H | 204–206 |
| 95 | CH=CH₂ | (CH₂)₄CH₃ | H | H | H | H | H | 78–79 |
| 96 | CH=CH₂ | —(CH₂)₉CH₃ | H | H | H | H | H | oil |
| 97 | CH=CH₂ | Cyclopentyl | H | H | H | H | H | 158–160 |
| 98 | CH=CH₂ | CH₂CF₃ | H | H | H | H | H | 151–153 |
| 99 | CH=CH₂ | CH=CH₂ | H | H | H | H | H | 153–156 |
| 100 | CH=CH₂ | CH₂CH=CHCH₃ | H | H | H | H | H | 103–105 - 85% trans isomer |
| 101 | CH=CH₂ | CH₂C(Br)=CH₂ | H | H | H | H | H | oil |
| 102 | CH=CH₂ | CH₂CH=CHCl | H | H | H | H | H | 104–106 - 90% trans isomer |
| 103 | CH=CH₂ | CH₂CH=CCl₂ | H | H | H | H | H | oil |
| 104 | CH=CH₂ | CH₂φ | H | H | H | H | H | 120–123 |
| 105 | CH=CH₂ | H | H | H | φ | H | H | 181–183 |
| 106 | CH=CH₂ | CH₂(4-Brφ) | H | H | H | H | H | oil |
| 107 | CH=CH₂ | ** | H | H | H | H | H | oil |
| 108 | CH=CH₂ | CH₃ | CH₃ | H | H | H | H | oil |
| 109 | CH=CH₂ | CH₂CH₃ | CH₃ | H | H | H | H | oil |
| 110 | CH=CH₂ | CH(CH₃)₂ | CH₃ | H | H | H | H | 118–120 |
| 111 | CH=CH₂ | (CH₂)₃CH₃ | CH₃ | H | H | H | H | 61–62 |
| 112 | CH=CH₂ | (CH₂)₂CH₃ | C₂H₅ | H | H | H | H | 101–102 |
| 113 | CH=CH₂ | CH(CH₃)₂ | C₂H₅ | H | H | H | H | oil |
| 114 | CH=CH₂ | CH₃ | —(CH₂)₁₁CH₃ | H | H | H | H | oil |
| 115 | CH=CH₂ | CH=CH₂ | CH₃ | H | H | H | H | oil |
| 116 | CH=CH₂ | CH=CH₂ | (CH₂)₂CH₃ | H | H | H | H | 147–150 |
| 117 | CH₂CH=CH₃ | CH₃ | H | H | H | H | H | 114–115 |
| 118 | CH₂CH=C(CH₃)₂ | H | H | H | H | H | H | oil |
| 119 | CH₃ | CH(CH₃)CH₂CH₃ | H | H | H | H | H | 143–145 |
| 120 | CH₂CH₃ | CH(CH₃)₂ | H | H | H | H | H | 135–137 |
| 121 | CH₂CH₂CH₃ | CH(CH₃)₂ | H | H | H | H | H | 122–123 |
| 122 | (CH₂)₃CH₃ | CH(CH₃)₂ | H | H | H | H | H | 80–82 |
| 123 | CH₃ | CH(CH₃)=CH₂ | H | H | H | H | H | 172–174 |
| 124 | CH₃ | CH₂C(O)OCH₃ | H | H | H | H | H | 139–140 |
| 125 | CH₃ | CH₂(4-NO₂φ) | H | H | H | H | H | 159–162 |
| 126 | CH=CH₂ | CH(CH₃)CH₂CH₃ | H | H | H | H | H | 114–115 |
| 127 | CH=CH₂ | CH(CH₃)=CH₂ | H | H | H | H | H | 149 |
| 128 | CH=CH₂ | CH₂CH₂OH | H | H | H | H | H | Oil |
| 129 | CH=CH₂ | CH₂C(O)OCH₃ | H | H | H | H | H | 149–151 |
| 130 | CH=CH₂ | CH₂(4-NO₂φ) | H | H | H | H | H | 141–144 |
| 131 | CH₃ | C(CH₃)₃ | H | H | H | H | H | 188–194 |
| 132 | CH=CH₂ | C(CH₃)₃ | H | H | H | H | H | 174–178 |
| 133 | CH₃ | Cyclopropyl | H | H | H | H | H | 171–173 |
| 134 | CH=CH₂ | Cyclopropyl | H | H | H | H | H | 159–161 |

*φ = Phenyl, for example, 4-Brφ = 4-bromophenyl.

**R¹ is 

EXAMPLE 7

The compounds identified in Table A hereinabove were tested for the preventative control of certain plant diseases by the procedures described below. The results of this testing is set forth in Table 1 hereinbelow, wherein Compound Numbers refer to the Compound Numbers assigned the respective compounds in Table A.

Tomato Late Blight (TLB)

Compounds of the invention were tested for the preventative control of the Tomato Late Blight organism *Phytophthora infestans*. Three to six week old tomato (cultivar Bonny Best) seedlings were used. The tomato plants were sprayed with either a 500 or 200 ppm suspension of the test compound in acetone, water and a non-ionic emulsifier. The sprayed plants were then inoculated 1 day later with the organism, placed in an environmental chamber and incubated at 66° F to 68° F and 100% relative humidity for 16 to 24 hours. Following the incubation, the plants were maintained in a greenhouse for approximately 7 days. The percent disease control provided by a given test compound was based on the percent disease reduction relative to untreated check plants.

The averaged results are reported in Table 1.

Rice Blast (RB)

Compounds of this invention were tested for control of the Rice Blast organism *Piricularia oryzae*, using 10 to 14 day old rice plant seedlings (Calrose M-9 variety). Seedling plants were sprayed with a 500 or 200 ppm solution of the test compound in acetone, water and a non-ionic emulsifier. The sprayed plants were inoculated 1 day later with the organism in an environmental chamber. After inoculation, the plants were kept in an environmental chamber for about 48 hours under conditions of about 72° F. to 75° F. and about 100% relative humidity. Following the incubation period, the plants were placed in a greenhouse with a temperature of about 80° F. and maintained with bottom watering for about 12 to 16 days. The percent disease control provided by a given test compound is based on a comparison of the percentage disease relative to the percent disease development on untreated check plants. The averaged results are reported in Table 1.

Celery Late Blight (CLB)

The Celery Late Blight tests were conducted using celery (Utah) plants 11 weeks old. The Celery Late Blight organism was *Septoria apii*. The celery plants were sprayed with either 500 or 200 ppm solutions of the test compound mixed with acetone, water and a nonionic emulsifier. The plants were then inoculated one day later with the organism and placed in an environmental chamber and incubated at 66° F. to 68° F. in 100% relative humidity for approximately 48 hours. Following the incubation, the plants were allowed to dry and then were maintained in a greenhouse for approximately 14 days. One plant was used per compound. Six untreated plants were used as the check for each screening group of compound. The percent disease control provided by a given candidate toxicant is based on the percent disease reduction relative to untreated check plants. The results are reported in Table 1.

Bean Powdery Mildew (BPM)

The compounds of the invention were tested for the control of the Bean Powdery Mildew organism, *Erysiphe polygoni*. Seedling bean plants were sprayed with a 500 or 200 ppm solution of the test compound in acetone, water and a nonionic emulsifier. The sprayed plants were then inoculated 1 day later with the organism. The plants were maintained for 10 days at temperatures of 68° F. at night with daytime temperatures of 72° F. to 80° F.; relative humidity was maintained at 40% to 60%. One plant was used per compound. Six untreated plants were used as the check for each screening group of compounds. The percent disease control provided by a given test compound was based on the percent disease reduction relative to the untreated check plants. The results are reported in Table 1.

Bean Rust (BR)

The Leaf Rust test was made using pinto beans. The pathogen was *Uromyces phaseoli tipica*. The bean plants were sprayed with either a 500 or 200 ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68° F. to 70° F. The plants were then removed from the chamber, allowed to dry, and then maintained in a greenhouse at a 60% to 80% relative humidity. The amount of infection on the leaves was rated after about 14 days. The percent disease control provided by a given test compound was based on the percent disease reduction relative to untreated check plants. The results are reported in Table 1.

TABLE 1

Preventative Fungicidal Activity
(Dosage rate 2.0 ppm unless otherwise indicated)
Percent Control

| COMPOUND NO. | TLB | RB | CLB | BPM | BR |
|---|---|---|---|---|---|
| 1 | 0 | 94 | 98 | 0 | 0 |
| 2* | 0 | 94 | 89 | 100 | 0 |
| 3* | 0 | 0 | 98 | 100 | 0 |
| 4* | 67 | 98 | 94 | 0 | 0 |
| 5* | 0 | 94 | 100 | 100 | 100 |
| 6 | 0 | 100 | 100 | 95 | 0 |
| 7* | 0 | 94 | 0 | 100 | 100 |
| 8* | 18 | 0 | 100 | 95 | 100 |
| 9* | 21 | 60 | 94 | 0 | 100 |
| 10 | 80 | 87 | 0 | 0 | 100 |
| 11* | 55 | 94 | 100 | 100 | 100 |
| 12* | 89 | 94 | 100 | 100 | 100 |
| 13 | 0 | — | 62 | 100 | 100 |
| 14 | 44 | 0 | 0 | 0 | 40 |
| 15 | 05 | — | 100 | 0 | 100 |
| 16 | 0 | 0 | 84 | 0 | 0 |
| 17 | 95 | 46 | 100 | 100 | 100 |
| 18 | 95 | 94 | 100 | 84 | 100 |
| 19 | 76 | 0 | 62 | 0 | 92 |
| 20 | 95 | 94 | 100 | 96 | 100 |
| 21 | 0 | 100 | 100 | 0 | 0 |
| 22 | 0 | 0 | 91 | 0 | 100 |
| 23 | 0 | — | 0 | 0 | 0 |
| 24 | 100 | 89 | 100 | 0 | 100 |
| 25 | 0 | 100 | 100 | 100 | 0 |
| 26 | 100 | 72 | 100 | 96 | 100 |
| 27 | 0 | 100 | 0 | 0 | 100 |
| 28 | 0 | 0 | 100 | 0 | 100 |
| 29 | 92 | 93 | 100 | 0 | 0 |
| 30 | 92 | 0 | 0 | 100 | 96 |
| 31 | 25 | — | 100 | 9 | 100 |
| 32 | 0 | 67 | 0 | 0 | 85 |
| 33 | 0 | 93 | 0 | 0 | 100 |
| 34 | 0 | 93 | 92 | 0 | 100 |
| 35 | 75 | 0 | 0 | 0 | 100 |
| 36 | 92 | 89 | 0 | 0 | 0 |
| 37 | 69 | 73 | 100 | 0 | 0 |
| 38* | — | 58 | 94 | 0 | — |
| 39 | 74 | 0 | 0 | 0 | 100 |
| 40 | 75 | 48 | 0 | 95 | 100 |
| 41 | 0 | 48 | 0 | 0 | 100 |
| 42 | 75 | 90 | 100 | 0 | 100 |
| 43 | 100 | 91 | 0 | 100 | 100 |
| 44 | 100 | 0 | 100 | 100 | 100 |
| 45 | 0 | 0 | 100 | 0 | 100 |
| 46 | 100 | 0 | 100 | 0 | 100 |
| 47 | 72 | 100 | 100 | 0 | 100 |
| 48 | 0 | 0 | 100 | 0 | 100 |
| 49* | — | 95 | 100 | 100 | — |
| 50* | 57 | 98 | 94 | 100 | 100 |

TABLE 1-continued

Preventative Fungicidal Activity
(Dosage rate 2.0 ppm unless otherwise indicated)
Percent Control

| COMPOUND NO. | TLB | RB | CLB | BPM | BR |
|---|---|---|---|---|---|
| 51* | 0 | 95 | 100 | 0 | 100 |
| 52 | 92 | 96 | 70 | 100 | 0 |
| 53 | 100 | 68 | 100 | 100 | 100 |
| 54 | 84 | 100 | 100 | 100 | 100 |
| 55 | 93 | 100 | 0 | 100 | 100 |
| 56 | 92 | 100 | 100 | 93 | 100 |
| 57 | 72 | 100 | 100 | 35 | 100 |
| 58 | 0 | 0 | 0 | 0 | 0 |
| 59 | 0 | 100 | 100 | 100 | 100 |
| 60 | 74 | 0 | 0 | 0 | 0 |
| 61 | 93 | 0 | 90 | 100 | 100 |
| 62 | 75 | 0 | 100 | 0 | 100 |
| 63 | 93 | 0 | 100 | 0 | 100 |
| 64 | 0 | 0 | 100 | 94 | 100 |
| 65 | 0 | 0 | 100 | 94 | 100 |
| 66 | 0 | 0 | 0 | 0 | 91 |
| 67 | 0 | 0 | 93 | 0 | 100 |
| 68 | 74 | 0 | 100 | 0 | 100 |
| 69 | 0 | 0 | 100 | 0 | 100 |
| 70 | 0 | 0 | 0 | 0 | 100 |
| 71 | 93 | 0 | 0 | 0 | 96 |
| 72 | 100 | 0 | 0 | 0 | 100 |
| 73* | 0 | 98 | 100 | 0 | 0 |
| 74 | 0 | 0 | 59 | 0 | 100 |
| 75 | 0 | — | 75 | 0 | 100 |
| 76* | 0 | 94 | 100 | 0 | 29 |
| 77* | 98 | 94 | 100 | 49 | 100 |
| 78 | 74 | 100 | 73 | 100 | 100 |
| 79 | 0 | — | 100 | 0 | 100 |
| 80* | 71 | 94 | 100 | 100 | 100 |
| 81* | 86 | 98 | 89 | 0 | 100 |
| 82 | 0 | 75 | 86 | 0 | 92 |
| 83* | 0 | 89 | 100 | 95 | 100 |
| 84 | 0 | 0 | 73 | 0 | 100 |
| 85 | 0 | 75 | 86 | 0 | 100 |
| 86 | 0 | 0 | 84 | 0 | 0 |
| 87 | 0 | 92 | 92 | 0 | 100 |
| 88 | 0 | 100 | 100 | 100 | 100 |
| 89 | 0 | 93 | 100 | 94 | 100 |
| 90 | 0 | 93 | 92 | 0 | 0 |
| 91 | 69 | 93 | 88 | 0 | 100 |
| 92 | 100 | 72 | 0 | 0 | 100 |
| 93 | 0 | 91 | 74 | 0 | 96 |
| 94 | 0 | 0 | 59 | 40 | 100 |
| 95 | 68 | 93 | 92 | 0 | 100 |
| 96 | 0 | 0 | 0 | 0 | 96 |
| 97 | 93 | 0 | 100 | 0 | 0 |
| 98 | 0 | 48 | 0 | 0 | 100 |
| 99 | 98 | 100 | 100 | 100 | 100 |
| 100 | 75 | 48 | 100 | 0 | 0 |
| 101 | 0 | 0 | 100 | 0 | 0 |
| 102 | 0 | 0 | 100 | 0 | 100 |
| 103 | 0 | 0 | 100 | 0 | 100 |
| 104* | 78 | 89 | 94 | 83 | 100 |
| 105* | — | 95 | 100 | 100 | — |
| 106* | 0 | 89 | 94 | 100 | 100 |
| 107 | 0 | — | 94 | 100 | 100 |
| 108 | 0 | 0 | 100 | 0 | 100 |
| 109 | 0 | — | 91 | 0 | 100 |
| 110 | 90 | 100 | 0 | 0 | 0 |
| 111 | 0 | 100 | 100 | 0 | 0 |
| 112 | 0 | 100 | 0 | 100 | 100 |
| 113 | 65 | 100 | 0 | 0 | 100 |
| 114 | 0 | — | 100 | 0 | 100 |
| 115 | 0 | 0 | 100 | 0 | 100 |
| 116 | 75 | 48 | 0 | 95 | 100 |
| 117 | 0 | 0 | 0 | 0 | 0 |
| 118 | 93 | 0 | 0 | 0 | 0 |
| 119 | 100 | 93 | 100 | 0 | 0 |
| 120 | 69 | — | 100 | 0 | 100 |
| 121 | 91 | — | 100 | 100 | 100 |
| 122 | 0 | — | 100 | 100 | 100 |
| 123 | 100 | — | 100 | 100 | 100 |
| 124 | 50 | 100 | 100 | 100 | — |
| 125 | 75 | 92 | 100 | 100 | — |
| 126 | 100 | — | 100 | 0 | 0 |
| 127 | 100 | 86 | 100 | 0 | 100 |
| 128 | 0 | 92 | 100 | 0 | 0 |
| 129 | 0 | 100 | 100 | 0 | — |
| 130 | 0 | 100 | 90 | 100 | — |
| 131 | 0 | 100 | 100 | — | 0 |
| 132 | 100 | 100 | 100 | — | 0 |
| 133 | 100 | 92 | 100 | — | 100 |
| 134 | | | | | |

*Dosage rate 500 ppm

EXAMPLE 8

The compounds indicated in Table 2 hereinbelow were tested on grape plants for the preventative control of grape downy mildew caused by *Plasmopara viticola*.

In this test, 5 to 6 week old *Vitis vinifera* "Emperor" grape seedlings were sprayed with a 716 micromolar aqueous solution of the test compound containing a small amount of acetone or acetone and water (50:50% by vol.) or dimethylformamide to aid solubility and a nonionic emulsifier. The plants were then placed in an environmental chamber and inoculated with the organisms and returned in the chamber for two days to ensure infection. The plants were then placed in standing water in a greenhouse maintained between 86° F. and 72° F. and relative humidity of 100% for ten days. The plants are then evaluated for disease development. Four to six plants were used for each test compound and evaluated against untreated plants (checks). Six check plants were used for each compound group tested. The percent disease control afforded by a given compound is based on the average disease reduction observed in the plants treated with the compound relative to the check plant average. These results are reported in Table 2 below. (Compound numbers refer to the compound number assigned the compound in Table A hereinabove.)

TABLE 2

Preventative Control of Grape Downy Mildew
(Dosage rate 716 μ molar unless otherwise indicated)

| COMPOUND NO. | % CONTROL | COMPOUND NO. | % CONTROL |
|---|---|---|---|
| 17 | 98 | 60 | 100 |
| 18 | 100 | 61 | 100 |
| 20 | 100 | 78 | 94 |
| 24 | 100 | 92 | 86 |
| 26 | 100 | 97 | 100 |
| 29 | 100 | 99* | 91 |
| 30 | 100 | 104** | 83 |
| 35 | 100 | 110 | 100 |
| 36 | 91 | 116 | 90 |
| 39 | 94 | 119 | 83 |
| 40 | 100 | 123** | 100 |
| 43 | 100 | 124** | 0 |
| 53 | 98 | 126** | 100 |
| 54 | 100 | 127** | 100 |
| 56 | 94 | 129** | 100 |
| 56 | | 130** | 100 |
| | | 131** | 100 |
| | | 132** | 100 |
| | | 133** | 100 |
| | | 134** | 100 |

*Dosage rate: 625 μ molar.
**Dosage rate: 200 ppm.

Obviously, many modifications and variations in the invention, described hereinabove and below, can be made without departing from the essence and scope thereof.

EXAMPLE 9

The compounds indicated in Table 3 hereinbelow were tested on Horsebean plants for the preventative control of Chocolate spot, induced by *Botrytis cineria*.

In this test, 2 to three week old Horsebean (*Vicia fava* "Longacre") plants were sprayed with a 625 micromolar aqueous solution of the test compound formulated in acetone, water, and a small amount on non-ionic surfactant. The following day, plants were inoculated with a spore suspension of the test fungus and placed in an environmental chamber maintained at 65° F. and 100% relative humidity. After three days, plants were evaluated for disease development. Four to six plants were used for each test compound and were evaluated against untreated plants (checks). Four to six check plants were used for each compound group tested. The percent disease control afforded by a given test compound is based on the average disease reduction observed in the plants treated with the compound relative to the untreated check plant average. The results are reported in Table 3 below. (Compound numbers refer to the compound number assigned the compound in Table A hereinabove).

TABLE 3

Preventative Control of *Botrytis cineria*
Induced Chocolate Spot in Beans
(Dosage rate 625 micromolar unless otherwise indicated)

| COMOUND NO. | % CONTROL | COMPOUND NO. | % CONTROL |
|---|---|---|---|
| 29 | 100 | 71 | 70 |
| 33 | 100 | 72 | 0 |
| 34 | 97 | 97 | 100 |
| 37 | 100 | 98 | 80 |
| 40 | 100 | 100 | 100 |
| 41 | 100 | 101 | 100 |
| 42 | 100 | 103 | 68 |
| 44 | 100 | 108 | 100 |
| 45 | 100 | 112 | 100 |
| 46 | 100 | 115 | 95 |
| 48 | 100 | 116 | 100 |
| 66 | 85 | 118 | 0 |
| 67 | 70 | 131 | 0 |
| 68 | 93 | 132 | 100 |
| 69 | 90 | 133 | 100 |
| 70 | 90 | 134 | 100 |

Obviously, many modifications and variations in the invention, described hereinabove and below, can be made without departing from the essence and scope thereof.

What is claimed is:

1. A compound having the formula:

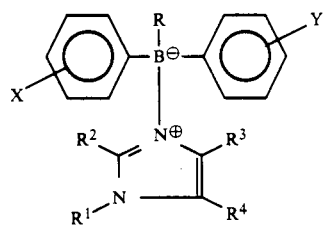

(I)

wherein:

R is alkyl having 1 through 4 carbon atoms; cycloalkyl having 3 through 6 carbon atoms; alkenyl having 2 through 6 carbon atoms; haloalkyl having 1 through 4 halo substituents independently selected from the group of fluoro, chloro and bromo; or haloalkenyl having 3 through 6 carbon atoms and 1 through 4 halo atoms independently selected from the group of fluoro, chloro, and bromo;

$R^1$ is hydrogen; alkyl having 1 through 12 carbon atoms; cycloalkyl having 3 through 6 carbon atoms; lower alkenyl having 2 through 6 carbon atoms; haloalkyl having 1 through 4 carbon atoms and 1 through 3 halo atoms independently selected from the group of fluoro, chloro, bromo, and iodo; haloalkenyl having 2 through 6 carbon atoms and 1 though 3 halo atoms independently selected from the group of fluoro, chloro, bromo, and iodo; cyanoalkyl wherein the alkyl moiety has 1 through 4 carbon atoms; hydroxyalkyl having 1 through 6 carbon atoms and 1 hydroxy group; lower alkoxyalkyl having 1 through 3 carbon atoms in the alkoxy moiety and 1 through 3 carbon atoms in the alkyl moiety; lower alkoxycarbonylalkyl having 1 through 3 carbon atoms in the alkoxy moiety and 1 through 3 carbon atoms in the alkyl moiety; phenyl; substituted phenyl having 1 through 4 substituents independently selected from the group of fluoro, chloro, bromo, iodo, lower alkyl having 1 through 6 carbon atoms and nitro with the proviso that said substituted phenyl has no more than two nitro substituents; aralkyl having 1 through 4 carbon atoms in the alkyl moiety and wherein the aryl moiety is phenyl; substituted benzyl having 1 through 4 substituents on the phenyl moiety independently selected from the group of fluoro, chloro, bromo, iodo, lower alkyl having 1 through 6 carbon atoms and nitro with the proviso the said phenyl moiety can have no more than 2 nitro substituents; and 1,3-dioxolan-2-yl-alkyl in which the alkyl moiety has 1 through 4 carbon atoms;

$R^2$ is hydrogen; lower alkyl having 1 through 6 carbon atoms; phenyl, benzyl, or substituted benzyl having 1 though 4 substituents on the phenyl ring independently selected from the group of fluoro, chloro, bromo, iodo and alkyl, having 1 through 6 carbon atoms;

$R^3$ is hydrogen or alkyl having 1 through 6 carbon atoms with the proviso that when $R^4$ is other than alkyl then $R^3$ is hydrogen;

$R^4$ is hydrogen, alkyl having 1 through 6 carbon atoms, phenyl, or phenalkyl in which the alkyl moiety has 1 through 4 carbon atoms; with the proviso that at least two of $R^1$, $R^2$, $R^3$ and $R^4$ are hydrogen and with the further proviso that when $R^3$ is alkyl, then $R^4$ is the identical parallel alkyl group; and X and Y are independently hydrogen; alkyl having 1 through 4 carbon atoms; fluoro; chloro; alkoxy having 1 through 4 carbon atoms; alkylthio having 1 through 4 carbon atoms; or haloalkyl having 1 through 4 carbon atoms and 1 through 3 halo substituents independently selected from the group of fluoro, chloro, and bromo; and may be located at any available position of the respective phenyl rings.

2. The compound of claim 1 wherein $R^2$, $R^3$ and $R^4$ are each hydrogen.

3. The compound of claim 1 wherein three of $R^1$, $R^2$, $R^3$ and $R^4$ are hydrogen.

4. The compound of claim 1 wherein R is alkyl, alkenyl, or haloalkenyl.

5. The compound of claim 4 wherein three of $R^1$, $R^2$, $R^3$ and $R^4$ are hydrogen.

6. The compound of claim 5 wherein R is methyl or vinyl.

7. The compound of claim 1 wherein $R^1$ is alkyl, cycloalkyl, alkenyl having 2 through 4 carbon atoms, 2-hydroxyethyl, or 2,2,2-trifluoroethyl.

8. The compound of claim 7 wherein R is methyl or vinyl.

9. The compound of claim 1 wherein $R^1$ is propyl, isopropyl, sec-butyl, t-butyl, cyclopropyl, vinyl, isopropenyl, 2-hydroxyethyl, or 2,2,2-trifluoroethyl.

10. The compound of claim 9 wherein R is methyl or vinyl.

11. The compound of claim 1 wherein X and Y are identical parallel substituents located at the same position of the respective phenyl rings to which they are attached.

12. The compound of claim 11 wherein $R^2$, $R^3$ and $R^4$ are each hydrogen.

13. The compound of claim 11 wherein three of $R^1$, $R^2$, $R^3$ and $R^4$ are hydrogen.

14. The compound of claim 11 wherein R is alkyl, alkenyl, or haloalkenyl.

15. The compound of claim 14 wherein three of $R^1$, $R^2$, $R^3$ and $R^4$ are hydrogen.

16. The compound of claim 15 wherein R is methyl or vinyl.

17. The compound of claim 11 wherein $R^1$ is alkyl, cycloalkyl, alkenyl having 2 through 4 carbon atoms, 2-hydroxyethyl, or 2,2,2-trifluoroethyl.

18. The compound of claim 17 wherein R is methyl or vinyl.

19. The compound of claim 17 wherein $R^2$, $R^3$ and $R^4$ are hydrogen

20. The compound of claim 11 wherein $R^1$ is propyl, isopropyl, sec-butyl, t-butyl, cyclopropyl, vinyl, isopropenyl, 2-hydroxyethyl, or 2,2,2-trifluoroethyl.

21. The compound of claim 20 wherein R is methyl or vinyl.

22. The compound of claim 20 wherein $R^2$, $R^3$ and $R^4$ are each hydrogen.

23. The compound of claim 11 wherein $R^2$, $R^3$ and $R^4$ are each hydrogen.

24. The compound of claim 11 wherein R is methyl or vinyl.

25. The compound of claim 11 wherein X and Y are each hydrogen.

26. The compound of claim 25 wherein $R^2$, $R^3$ and $R^4$ are each hydrogen.

27. The compound of claim 25 wherein three of $R^1$, $R^2$, $R^3$ and $R^4$ are hydrogen.

28. The compound of claim 25 wherein R is alkyl, alkenyl, or haloalkenyl.

29. The compound of claim 28 wherein three of $R^1$, $R^2$, $R^3$ and $R^4$ are hydrogen.

30. The compound of claim 29 wherein R is methyl or vinyl.

31. The compound of claim 25 wherein $R^1$ is alkyl, cycloalkyl, alkenyl having 2 through 4 carbon atoms, 2-hydroxyethyl or 2,2,2-trifluoroethyl.

32. The compound of claim 31 wherein R is methyl or vinyl.

33. The compound of claim 31 wherein $R^2$, $R^3$ and $R^4$ are each hydrogen.

34. The compound of claim 25 wherein $R^1$ is propyl, isopropyl, sec-butyl, 2-hydroxyethyl, t-butyl, cyclopropyl, vinyl, isopropenyl or 2,2,2-trifluoromethyl.

35. The compound of claim 34 wherein R is methyl or vinyl.

36. The compound of claim 34 wherein $R^2$, $R^3$ and $R^4$ are each hydrogen.

37. The compound of claim 36 wherein R is methyl or vinyl.

38. The compound of claim 25 wherein $R^1$ is isopropenyl.

39. The compound of claim 38 wherein $R^2$, $R^3$ and $R^4$ are each hydrogen and R is methyl or ethyl.

40. The compound of claim 37 wherein said compound is (1-sec-butylimidazole)-diphenylvinylborane.

41. The compound of claim 37 wherein said compound is (1-propylimidazole)-diphenylmethylborane.

42. The compound of claim 37 wherein said compound is (1-isopropylimidazole)-diphenylmethylborane.

43. The compound of claim 37 wherein said compound is (1-t-butylimidazole)-diphenylmethylborane.

44. The compound of claim 37 wherein said compound is (1-cyclopropylimidazole)-diphenylmethylborane.

45. The compound of claim 37 wherein said compound is (1-t-butylimidazole)-diphenylvinylborane.

46. The compound of claim 37 wherein said compound is (1-cyclopropylimidazole)-diphenylvinylborane.

47. The compound of claim 37 wherein said compound is (1-vinylimidazole)-diphenylvinylborane.

48. The compound of claim 1 wherein $R^1$ is hydrogen, alkyl having 1 through 6 carbon atoms, alkenyl, haloalkenyl, phenyl or phenalkyl; $R^2$, $R^3$, and $R^4$ are independently hydrogen or methyl, ethyl, n-propyl or isopropyl, and X and Y are each hydrogen.

49. The compound of claim 1 wherein R is methyl or vinyl.

50. The compound of claim 1 wherein $R^1$ is 1,3-dioxolan-2-ylalkyl.

51. The compound of claim 11 wherein $R^1$ is 1,3-dioxolan-2-yl-alkyl.

52. The compound of claim 1 wherein at least one of $R^1$ or $R^2$ is substituted benzyl.

53. The compound of claim 11 wherein at least one of $R^1$ or $R^2$ is substituted benzyl.

54. The compound of claim 1 wherein said compound is (1-2'-hydroxyethylimidazole)-diphenylvinylborane.

55. The compound of claim 1 wherein said compound is (1-sec-butylimidazole)-diphenylmethylborane.

56. A fungicidal composition comprising a fungicidally effective amount of the compound claim 1 and a compatible carrier.

57. A fungicidal composition comprising a fungicidally effective amount of the compound claim 37 and a compatible carrier.

58. A fungicidal composition comprising a fungicidally effective amount of the compound claim 42 and a compatible carrier.

59. A fungicidal composition comprising a fungicidally effective amount of the compound claim 47 and a compatible carrier.

60. A fungicidal composition comprising a fungicidally effective amount of the compound of claim 55 and a compatible carrier.

61. A method for controlling fungi which comprises contracting said fungi or its habitats with a fungicidally effective amount of a compound according to claim 1.

62. A method for controlling fungi which comprises contracting said fungi or its habitats with a fungicidally effective amount of a compound according to claim 37.

63. A method for controlling fungi which comprises contracting said fungi or its habitats with a fungicidally effective amount of a compound according to claim 42.

64. A method for controlling fungi which comprises contracting said fungi or its habitats with a fungicidally effective amount of a compound according to claim 47.

65. A method for controlling fungi which comprises contacting said fungi or its habitats with fungicidally effective amount of the compound of claim 55.

* * * * *

UNITED STATES PATENT AND TRADEMARK OFFICE
CERTIFICATE OF CORRECTION

PATENT NO. : 4,983,589

DATED : January 8, 1991

INVENTOR(S) : Tsze H. Tsang, Vincent J. Spadafora, and Patricia Pomidor

It is certified that error appears in the above-identified patent and that said Letters Patent is hereby corrected as shown below:

Column 40, line 26, "2.0 ppm" should read --200 ppm--.

Column 41, line 3, "2.0 ppm" should read --200 ppm--.

Column 42, line 3, "2.0 ppm" should read --200 ppm--.

Signed and Sealed this

First Day of September, 1992

Attest:

DOUGLAS B. COMER

Attesting Officer

Acting Commissioner of Patents and Trademarks